United States Patent [19]
Lee et al.

[11] Patent Number: 5,541,223
[45] Date of Patent: * Jul. 30, 1996

[54] 4β-AMINO PODOPHYLLOTOXIN ANALOG COMPOUNDS AND METHODS

[75] Inventors: Kuo-Hsiung Lee, Chapel Hill, N.C.; Yung-Chi Cheng, Woodbridge, Conn.

[73] Assignees: Yale University, New Haven, Conn.; The University of North Carolina at Chapel Hill, Chapel Hill, N.C.

[*] Notice: The portion of the term of this patent subsequent to Jul. 21, 2009, has been disclaimed.

[21] Appl. No.: 145,382

[22] Filed: Oct. 28, 1993

Related U.S. Application Data

[63] Continuation of Ser. No. 874,345, Apr. 24, 1992, abandoned, which is a continuation-in-part of Ser. No. 313,826, Feb. 23, 1989, abandoned, and Ser. No. 406,330, Sep. 12, 1989, Pat. No. 5,132,322.

[51] Int. Cl.$^6$ ............... A61K 31/36; A61K 31/365; C07D 307/77
[52] U.S. Cl. ............... 514/468; 514/313; 514/314; 514/338; 514/463; 546/173; 546/174; 546/283.7; 549/298; 549/358; 549/432
[58] Field of Search ............... 549/298, 358, 549/432; 546/173, 174, 270; 514/313, 314, 338, 463, 468

[56] References Cited

U.S. PATENT DOCUMENTS 5,132,322  7/1992  Lee et al. ............... 549/298

FOREIGN PATENT DOCUMENTS 88-068417/10  7/1986  Japan.
88-053946/08  7/1986  Japan.
89-153953/21  5/1987  Japan.
89-181291/25  10/1987  Japan.
1-197486  of 1989  Japan.
WO90/09788  9/1990  WIPO.

OTHER PUBLICATIONS

Ayres, D. C., and Lim, C. K., "Modification of the Pendant Ring of Podophyllotoxin," *Cancer Chemother. Pharmacol.* 7:99–101.
Chen, G. L., et al., "Nonintercalative Antitumor Drugs Interfere with the Breakage–Reunion Reaction of Mammalian DNA Topoisomerase II," *J. Biol. Chem.* 259(21):13560–13566 (1987).
Lee, K. H., et al., "Antitumor Agents, 107, New Cytotoxic 4–Alkylamino Analogues of 4'–Demethyl–epipodophyllotoxin as Inhibitors of Human DNA Topoisomerase II," *J. Natur. Prod.* 52(3):606–613 (1989).
Liu, L. F., et al., "Novel topologically knotted DNA from bacteriophage P4 capsids: studies with DNA topoisomerases," *Nuc. Acids Res.* 9(16):3979–3989 (1981).
Maxwell, A., and Gellert, M., "Mechanistic Aspects of DNA Topoisomerases," *Adv. Protein Chem.* 38:69–107 (1986).
Minocha, A., and Long, B. H., "Inhibition of the DNA Catenation Activity of Type II Topoisomerase by VP16–213 and VM26," *Biochem. Biophys. Res. Comm.* 122(1):165–170 (1984).
Ross, W., et al., "Role of Topoisomerase II in Mediating Epipodophyllotoxin–induced DNA Cleavage," *Cancer Res.* 44:5857–5860 (1984).
Rowe, T. C., et al., "DNA Damage by Antitumor Acridines Mediated by Mammalian DNA Topoisomerase II," *Cancer Res.* 46:2021–2026 (1986).
Rowe, T., et al., "Inhibition of Epipodophyllotoxin Cytotoxicity by Interference with Topoisomerase–Mediated DNA Cleavage," *Biochem. Pharmacol.* 34(14):2483–2487 (1985).
Thurston, L. S., et al., "Antitumor Agents. 78. Inhibition of Human DNA Topoisomerase II by Podophyllotoxin and α–Peltatin Analogues," *J. Med. Chem.* 29:1547–1550 (1986).
Thurston, L. S., et al., "Antitumor Agents. 100. Inhibition of Human DNA Topoisomerase II by Cytotoxic Ether and Ester Derivatives of Podophyllotoxin and α–Peltatin," *J. Med. Chem.* 32:604–608 (1989).
Wang, J. C., "DNA Topoisomerases," *Ann. Rev. Biochem.* 54:665–697 (1985).
Lee et al, "J. Med. Chem., " 33(5), pp. 1364–1368, 1990.
Wang et al, "J. Med. Chem.,", 33(9), pp. 2660–2666, 1990.
Chang et al, "Cancer Research", 51, pp. 1755–1759, 1991.

*Primary Examiner*—C. Warren Ivy
*Assistant Examiner*—Ba K. Trinh
*Attorney, Agent, or Firm*—Peter J. Dehlinger; Vincent M. Powers

[57] ABSTRACT

Novel podophyllotoxin compounds and their use in treating tumors are disclosed. The analogs have the general formula:

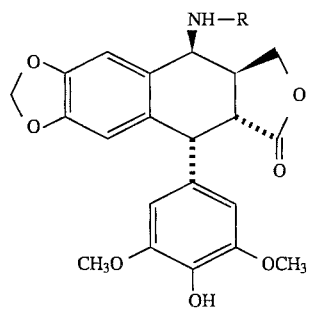

wherein NH—R is a selected aryl amine, dialkylaminoalkyleneamino, or dialkylaminoanilino group.

10 Claims, 9 Drawing Sheets

(4-a)

(4-g)

(4-b)

(4-h)

(4-c)

(4-i)

(4-d)

(4-j)

(4-e)

(4-k)

(4-f)

(4-l)

(2)

(19)

(15)

4β-AMINO PODOPHYLLOTOXIN ANALOG COMPOUNDS AND METHODS

This is a continuation of application Ser. No. 07/874,345, filed Apr. 24, 1992, now abandoned, which is a continuation-in-part of U.S. patent applications for (i) "Etoposide Analogues", Ser. No. 07/313,826, filed Feb. 23, 1989, now abandoned, and (ii) "Etoposide Analogs", Ser. No. 07/406,330, filed Sep. 12, 1989, now U.S. Pat. No. 5,132,322.

FIELD OF THE INVENTION

The present invention relates to novel 4β-amino podophyllotoxin analog compounds useful in the treatment of tumors, to methods of synthesis of the compounds, and to methods of treating tumors with pharmaceutical preparations containing the compounds.

References

Ayers, et al., Cancer Chemother Pharmacol, 7:99 (1980).
Chen, G. L., et al., J Biol Chem, 259:13560 (1984).
Hansch, C., et al., Substituent Constants for Correlation Analysis in Chemistry and Biology, Chapter III, Wiley-Interscience, New York (1979).
Lee, K. H., et al., J Nat Prod, 52:606 (1989).
Liu, L. F., et al., Nucleic Acid Res, 9:3979 (1981).
Maxwell, A., et al., Adv Protein Chem, 38:69 (1986).
Minocha, A., et al., Biochem Biophys Res Commun, 122:165 )1984).
Ross, W., et al., Cancer Res, 44:5857 (1984).
Rowe, R. C., et al., Cancer Res, 46:2021 (1986).
Rowe, T., et al., Biochem. Pharmacol, 34:2483 (1985).
Thurston, L. S., et al., J Med Chem, 29:1547 (1986).
Thurston, L. S., et al., J Med Chem, 31 (1988).
Wang, J. C., Ann Rev Biochem, 54:665 (1985).
Wang, Z-Q., et al, J Med Chem, 33:1364 (1990a).
Wang, Z-Q., et al, J Med Chem, 33:2660 (1990b).

BACKGROUND OF THE INVENTION

Podophyllotoxin is a naturally occurring compound extracted from the mandrake plant. Recently a therapeutically useful semi-synthetic glycoside of podophyllotoxin, etoposide (also known as VP-16), shown below, has been developed.

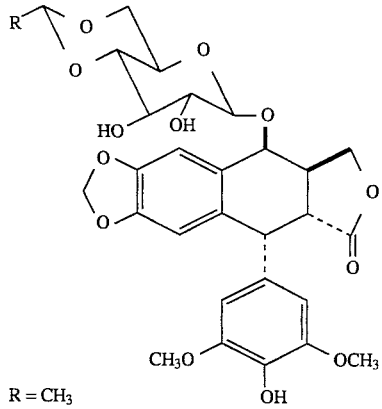

R = CH$_3$

This compound exhibits therapeutic activity in several human neoplasms, including small cell carcinomas of the lung, testicular carcinomas, Hodgkin's disease, leukemia, lymphoma and Kaposi's Sarcoma.

It is believed that these drugs block the catalytic activity of DNA topoisomerase II by stabilizing an enzyme-DNA complex in which the DNA is cleaved and covalently linked to the enzyme (Chen, Ross, Rowe), which are all herein specifically incorporated by reference. By way of background, topoisomerases are enzymes which control the topological state of DNA. Type II topoisomerases catalyze DNA strand passage through transient double strand breaks in the DNA. The resulting change in the linking number of DNA allows these enzymes to mediate DNA interconversions, such as supercoiling and relaxation of supercoiling, catenation and decatenation, knotting, and unknotting (Wang, 1985, Maxwell).

Type II DNA topoisomerase enzymes have been shown to be involved in a number of vital cellular processes, including DNA replication and transcription, and chromosomal segregation. These enzymes, therefore, are a critical target for the action of a wide variety of anticancer drugs, including etoposide. The key step leading to cell death may be the capability of these drugs to block the catalytic activity of DNA topoisomerase II, as noted above.

Structure-activity studies have demonstrated a direct correlation between cytotoxicity, DNA breakage, and murine-derived topoisomerase II inhibition activities among the podophyllotoxin analogues (Minocha). The isolation and purification of human type II topoisomerase from lymphocytic leukemia cells has provided the means to use this enzyme as a target to investigate the structure-related activity relationships among etoposide and related congeners.

It has been shown that the substitution of etoposide's glycosidic moiety by an 4-alkoxy group, as in 4'-demethylepipodophyllotoxin ethyl ether, preserves the inhibitory activity of DNA topoisomerase II intact at higher concentrations (Thurston, 1986). However, it has also been shown that a series of 4-acyl congeners are less active, even though some of them possessed potent cytotoxicity (Thurston, 1988).

Although etoposide has been widely used at the clinical level, the development of drug resistance, myelosuppression, and poor oral bioavailability has encouraged synthesis of analogues related to etoposide which possess preferred pharmacological profiles. Previous studies by the inventors were directed at substituted amino analogs. These analogs are disclosed in U.S. patent application 07/313,826, filed Feb. 23, 1989, hereby incorporated by reference. These compounds have also been disclosed by the applicants in the literature (Wang, 1990a, 1990a), and these references are also incorporated herein by reference. The compounds described therein have yielded numerous useful compositions which can be converted to water soluble products. Not only are many of these compounds more potent than etoposide in the inhibition of human DNA topoisomerase II and in causing protein linked DNA breakage, but these compounds also display activity against KB resistant cells.

Other etoposide analogs which posses anti-cancer activity have been disclosed in Japanese patent No. H1 -197486 (August 9, 1989). The Japanese patent discloses compounds of the following formula:

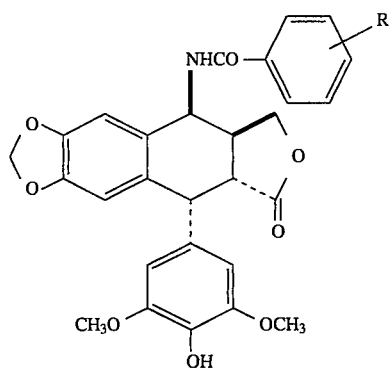

wherein R is a sugar moiety selected from arabinosyl, xyrosyl, rhamnosyl, glucosyl, and 4,6-ethylene glucosyl. This patent also discloses a synthetic method for the intermediate of the formula:

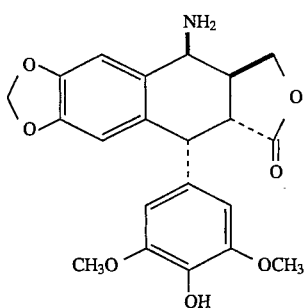

Improved methods for the production of this compound have been disclosed (e.g., Lee).

Another podophyllotoxin derivative synthesized in the art is 3',4'-didemethoxy-3',4'-dioxopodophyllotoxin of formula:

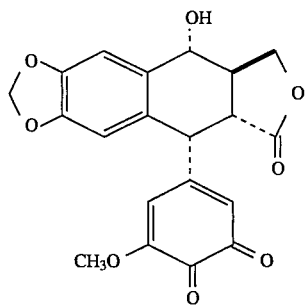

Ayers et al. (1980) disclosed the synthesis of this compound by reacting podophyllotoxin with nitric acid. Nemec discloses a similar oxidation of etoposide-3',4'-orthoquinone, and related compounds, in U.S. Pat. No. 4,609,664 using sodium periodate as an oxidizing agent.

SUMMARY OF THE INVENTION

The present invention includes, in one aspect, novel 4β-amino podophyllotoxin analog compounds of the general formula:

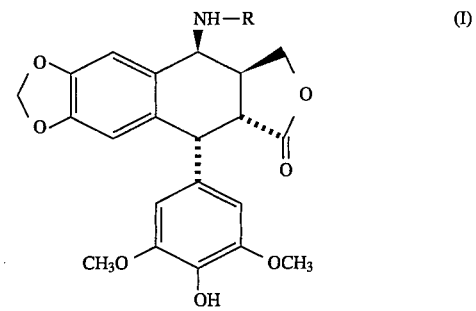

wherein NH—R has one of the following general structures:

(a) $NH-(CH_2)_n-NR_1R_2$, (b) 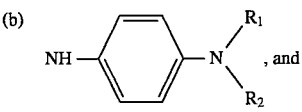

(c) one of the aryl amines 4-a to 4-t shown in FIG. 2, including ammonium salts of the structures (a), (b), and (c), where $R_1$ and $R_2$ in structures (a) and (b) may be H on lower alkyl groups.

Also disclosed are methods of synthesizing the 4β-amino podophyllotoxin analogs corresponding to structures (a) and (b), and methods of their use in treating tumors, as well as pharmaceutical compositions containing the compounds for use in tumor treatment.

These and other objects and features of the present invention will become more fully apparent when the following detailed description of the invention is read in conjunction with the accompanying drawings.

DETAILED DESCRIPTION OF THE INVENTION

The present invention includes novel 4β-amino podophyllotoxin analog compounds of the general formula:

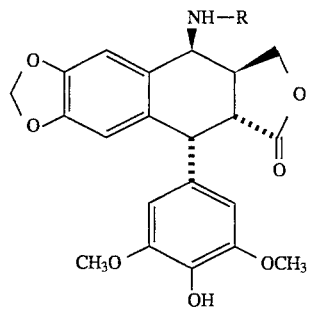

The parent structure shown is a 4'-O-demethyl epipodophyllotoxin, meaning a podophyllotoxin parent structure in which the 4' methoxy group of podophyllotoxin has been substituted by an OH group. The invention also contemplates analogous compounds in which the 3', 4', and or 5' positions on the phenyl ring are OH, methoxy, or ethoxy groups. In the compounds of the invention, a selected amino group, indicated at NH—R, is carried at the 4β position of the fused ring portion of the structure, as shown.

In one embodiment, described in Section 1, the 4β-amino group is an aryl amine selected from one of the moieties shown in FIG. 2. In a second general embodiment, illustrated in Section II, the amine has the general form —NH—$(CH_2)_n NR_1 R_2$, (dialkylaminoalkyleneamine), where $R_1$ and $R_2$ are H or lower alkyl groups, and n=2–4. Section III describes dialkylaminoanilino analogs.

I. Arylamine Podophyllotoxin Analog Compounds

FIG. 2 shows aryl amino (NH—R) moieties in 4β-amino podophyllotoxin analog compounds (4-a)–(4-t) of the invention. Compounds (4-a)–(4-n) are substituted aniline podophyllotoxin compounds disclosed in the parent patent application for "Etoposide Analogs", Ser. No. 07/406,330, filed Sep. 12, 1989. Compounds (4-o) and (4-p) are 2" and 3"-pyridylamino podophyllotoxin compounds, respectively, also disclosed in the above parent patent application. Compound (4-q) is a 3" quinolylamino podophyllotoxin compound, also disclosed in the above parent patent application. Compounds (4-r)–(4-t) are hydrochloride salts of three amino anilino podophyllotoxin compounds which are disclosed in the above parent patent application, and whose salts are disclosed in a parent patent application for "New Etoposide Analogs".

A. Compound Synthesis

Figure 1:
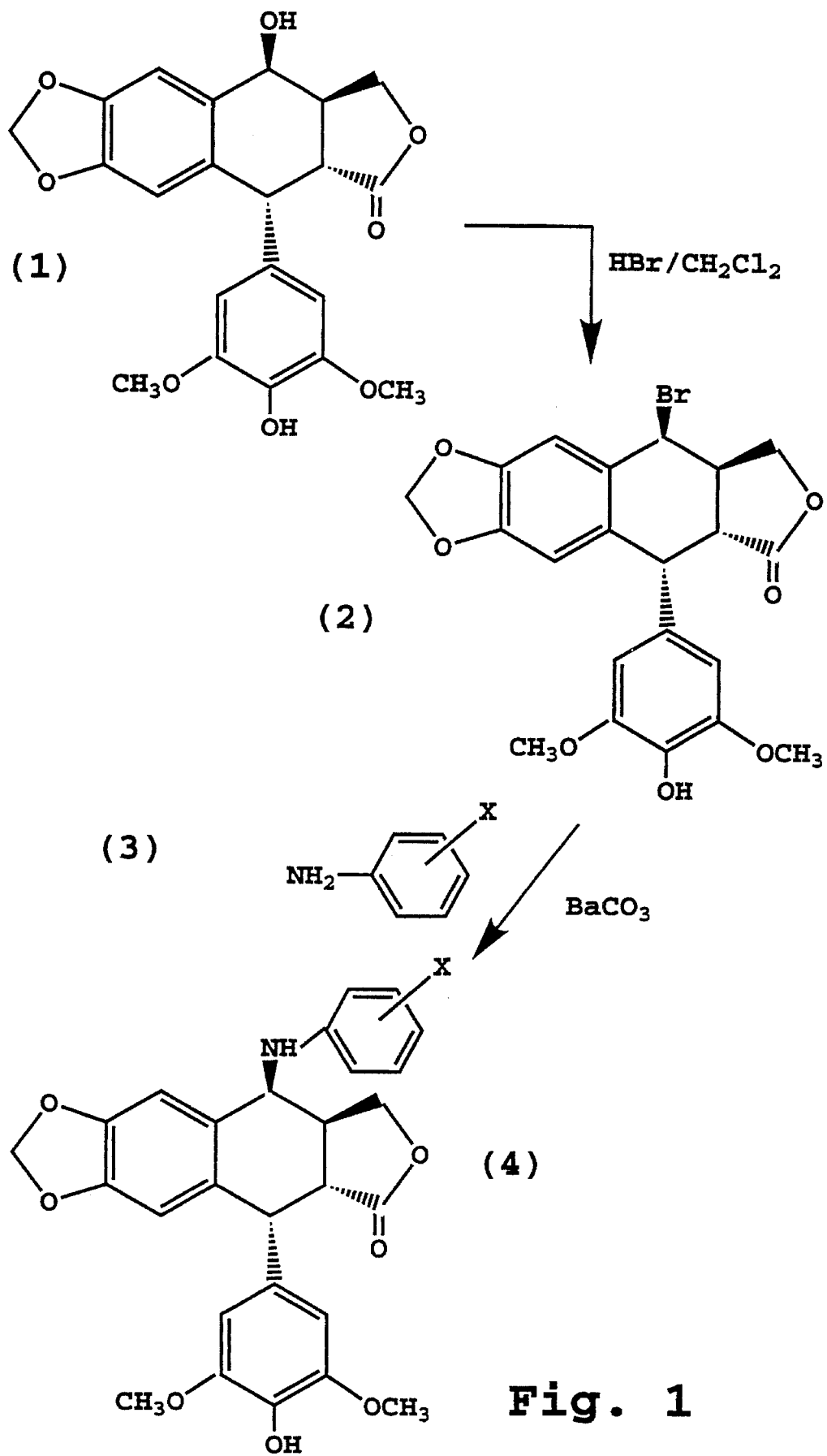
FIG. 1 shows steps in the general synthesis of aryl amine podophyllotoxin analog compounds of the type illustrated by compound 4 in FIG. 2.
Figure 2A:
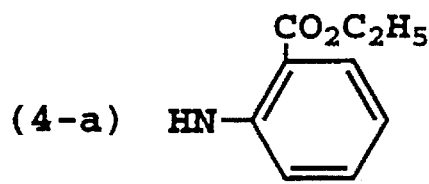
FIG. 2 shows the aryl amine moiety in 4β-arylamino podophyllotoxin analog compounds 4-a to 4-t, in accordance with one general embodiment of the invention.
Figure 2A:
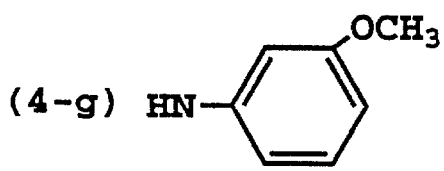
Figure 2A:
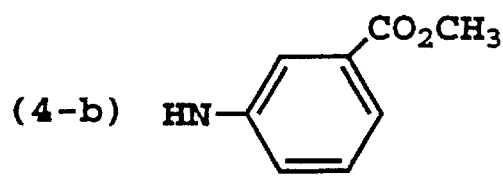
Figure 2A:
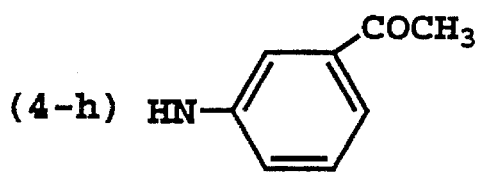
Figure 2A:
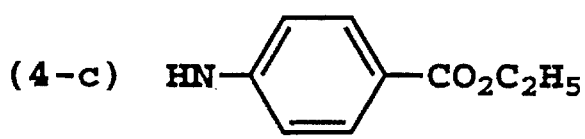
Figure 2A:
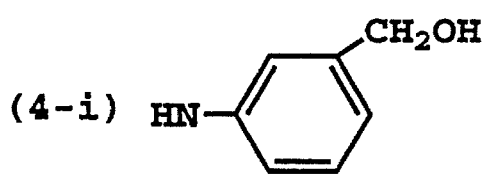
Figure 2A:
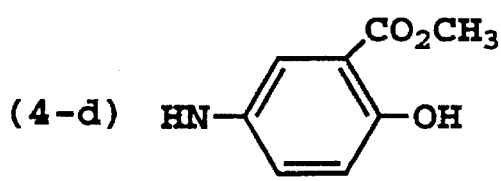
Figure 2A:
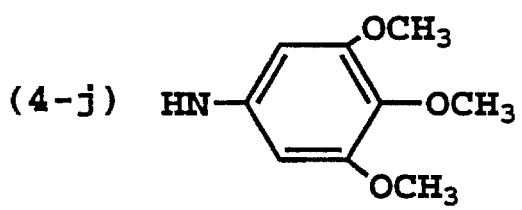
Figure 2A:
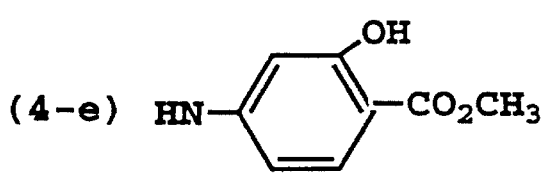
Figure 2A:
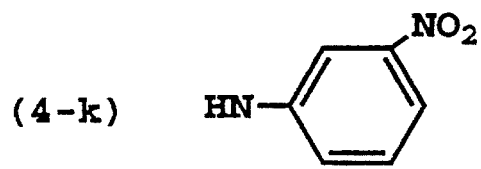
Figure 2A:
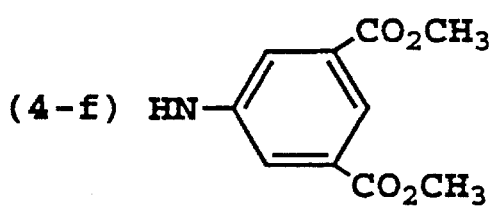
Figure 2A:
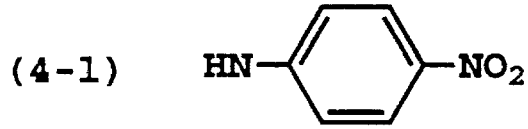
Figure 2B:
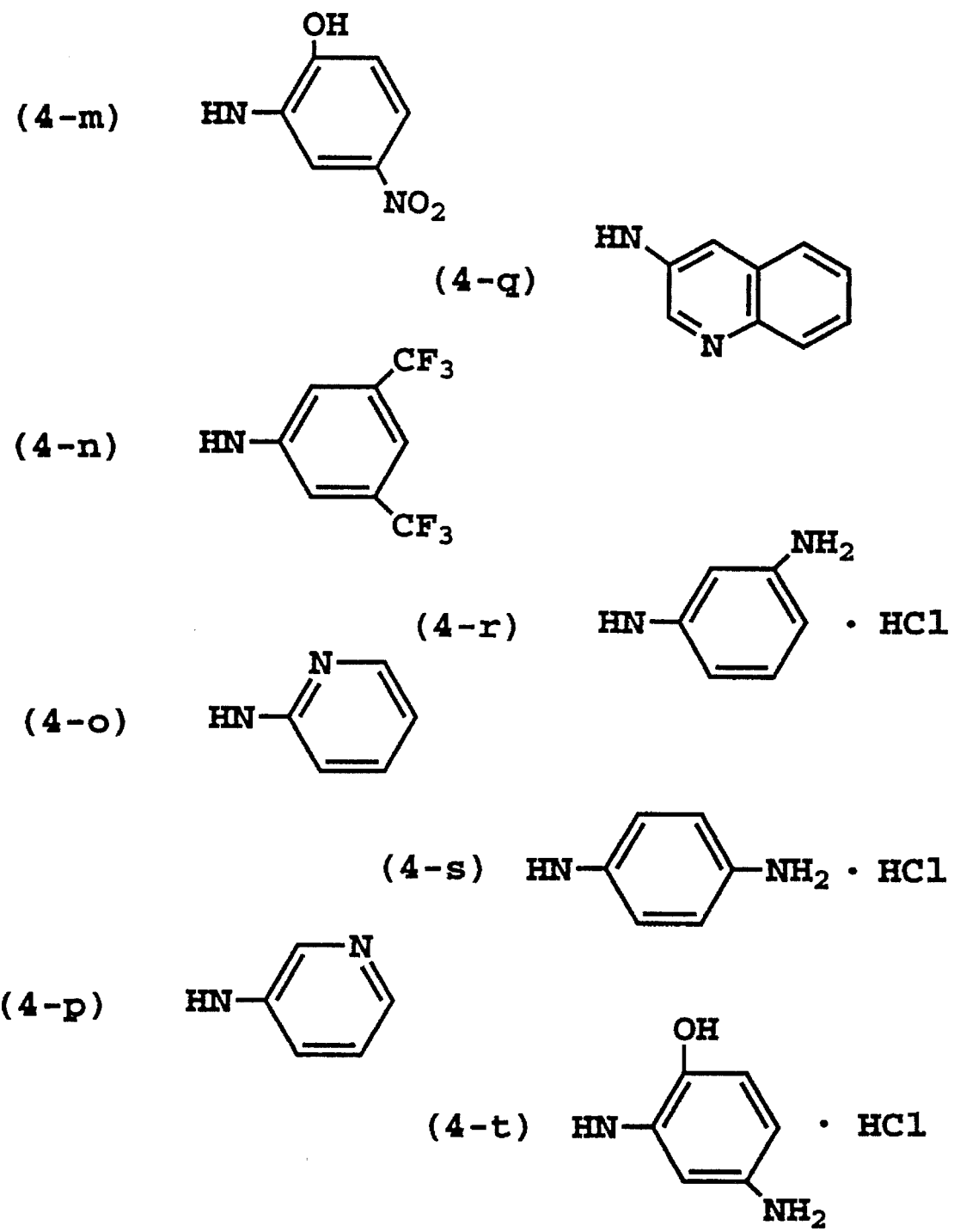

The compounds in FIG. 2 are easily synthesized according to the synthetic steps outlined in FIG. 1, and detailed in Example 1. Briefly, with reference to FIG. 1, HBr gas is bubbled through a solution of podophyllotoxin, i.e., 4"-O-Demethylepipodophyllotoxin (compound 1) in dry dichloromethane, followed by bubbling nitrogen to drive off excess HBr, forming the corresponding 4'-O-Demethyl-4β-bromo-4-desoxypodophyllotoxin (compound 2). The solution of compound 2 is evaporated under vacuum, and water is removed using benzene as an azeotropic mixture.

To form the desired aryl amine, compound 2 is combined with anhydrous barium carbonate, and the appropriate arylamine, indicated generally by compound 3, in dry 1,2-dichloroethane under nitrogen. After stirring overnight at room temperature, the reaction mixture is filtered, diluted with ethyl acetate, washed with water, dried over anhydrous magnesium sulfate, and purified via column chromatography, as detailed in Example 1. The aryl amine product is shown generally as a substituted aniline group (compound 4), although other aryl amines (compounds (4-a)–(4-q) in FIG. 2) are contemplated.

Compounds (4-r)–(4-t) can be formed as described in Example 2. Here a solution of compound (4-k), (4-l) or (4-m) in ethyl acetate is adjusted with HCl in methanol to pH=1–2, and mixed with 10% palladium on activated carbon, with stirring under hydrogen. After removing the catalyst by filtration, the filtrate and washings are combined and evaporated to give a solid, which is washed with ether to remove excess HCl.

More generally, the ammonium salts of compounds 4-r, 4-s, and 4-t can be formed by reacting the parent compound with a stoichiometric amount of an acid to form the corresponding water-soluble ammonium salt. Inorganic acids and organic acids capable of forming a water-soluble salt with the aryl amine compounds are physiologically acceptable and are selected, for example, from hydrochloride acid, hydrobromic acid, hydroiodic acid, sulfuric acid, phosphoric acid, nitric acid, acetic acid, propionic acid, formic acid, 1-ascorbic acid, tartaric acid, citric acid, lactic acid, maleic acid, fumaric acid, methanesulfonic acid, toluenesulfonic acid and benzenesulfonic acid. Ammonium salts of compounds 4-a to 4-t, where the bridging aryl amine is the protonated salt species are also contemplated.

B. Properties

Compounds (4-a)–(4-t) have been tested for inhibition of DNA topoisomerase II, and for the formation of intracellular formation of covalent topoisomerase II-DNA complexes, according to published methods (Lee, 1989), and as described in Examples 6A and 6B, respectively. Table I below gives the results of the biological evaluations. Cytotoxicity, expressed as $ID_{50}$, is the concentration of analog compound which gives a 50% reduction in cell number of $10^4$ cells after three days incubation. Each compound was examined with five concentrations, at 5, 10, 25, 50, and 100 μM. The $ID_{50}$ value was established on the basis of the degree of inhibition at these concentrations.

TABLE 1

| compd | cytotoxicity $ID_{50}$ KB, μM | inhibition of DNA topoisomerase II activity. $ID_{50}$, μM | cellular protein-DNA complex formation, % (10 μM) |
|---|---|---|---|
| 4-a | 1.0 | >100 | 4 |
| 4-b | 2.7 | 50 | 249 |
| 4-c | 0.84 | 5 | 207 |
| 4-d | 1.0 | 50 | 83 |
| 4-e | 5.8 | 50 | 129 |
| 4-f | <1.0 | 25 | 50 |
| 4-g | 3.8 | 25 | 104 |
| 4-h | 1.7 | 50 | 150 |
| 4-i | <1.0 | 25 | 235 |
| 4-j | 0.63 | >100 | 47 |
| 4-k | 1.0 | 50 | 230 |
| 4-l | 0.49 | 10 | 323 |
| 4-m | 1.0 | >100 | 15 |
| 4-n | 3.4 | >100 | 21 |
| 4-o | 0.71 | 50 | 97 |
| 4-p | 0.24 | 50 | 148 |
| 4-q | <1.0 | 50 | 123 |
| 4-r | 4.0 | 25 | 140 |

TABLE 1-continued

| compd | cytotoxicity ID$_{50}$ KB, μM | inhibition of DNA topoisomerase II activity. ID$_{50}$, μM | cellular protein-DNA complex formation, % (10 μM) |
|---|---|---|---|
| 4-s | 0.8 | 5 | 330 |
| 4-t | 3.3 | >100 | 11 |

As seen, the compounds most active in inhibiting topoisomerase II were compounds in which the aniline group was substituted at the para position with a $CO_2CH_2CH_3$ (4-c), $NO_2$ (4-l), or $NH_2 \cdot HCl$ (4-s) group. These three compounds are preferred embodiments in the present embodiment of the invention, with the para nitro substituted compound (4-l) being particularly preferred. These three substituents cover a broad range of electronegativity, as measured by published Hammett values (Hansch), and all are relatively water soluble, as measured by published π (water/octanol partition coefficients) (Hansch).

II. Dialkylaminealkylamino Podophyllotoxin Analog Compounds

In the compounds described in this section, the 4βNH—R group has the general form NH—$(CH_2)_n$—$NR_1R_2$, where $R_1$ and $R_2$ are H or lower alkyl groups, meaning 1–4 carbon alkyl groups, and where the $R_1$ and $R_2$ chains may be linked, e.g., to form a pyrolidone ring. Exemplary compounds in this embodiment are shown in FIGS. 4A–4B, and discussed below.

Figure 3A:
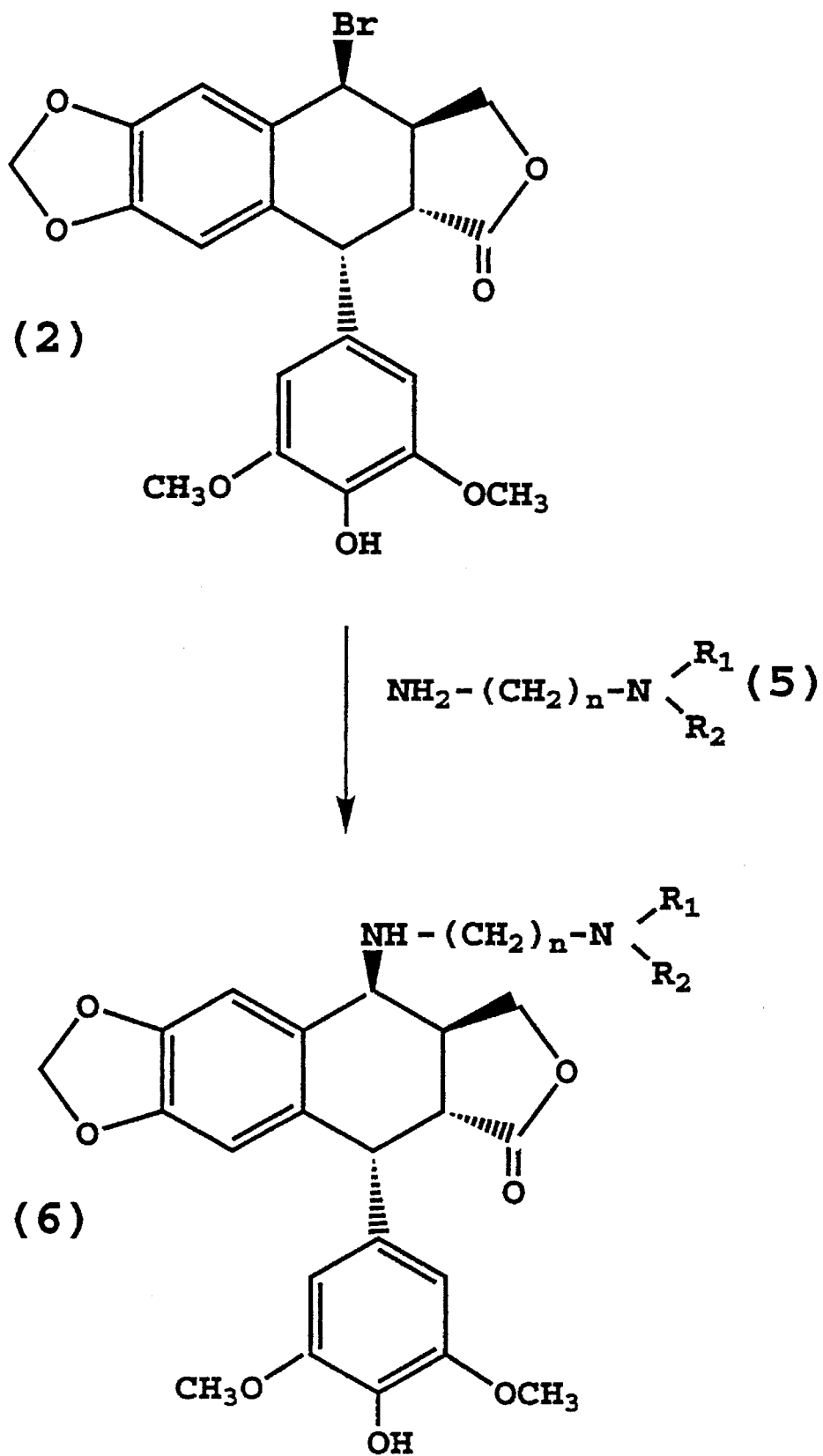
FIG. 3A shows steps in one method of synthesis of 4β-aminoalkyl podophyllotoxin analog compounds of the type illustrated by compound 6.
Figure 3B:
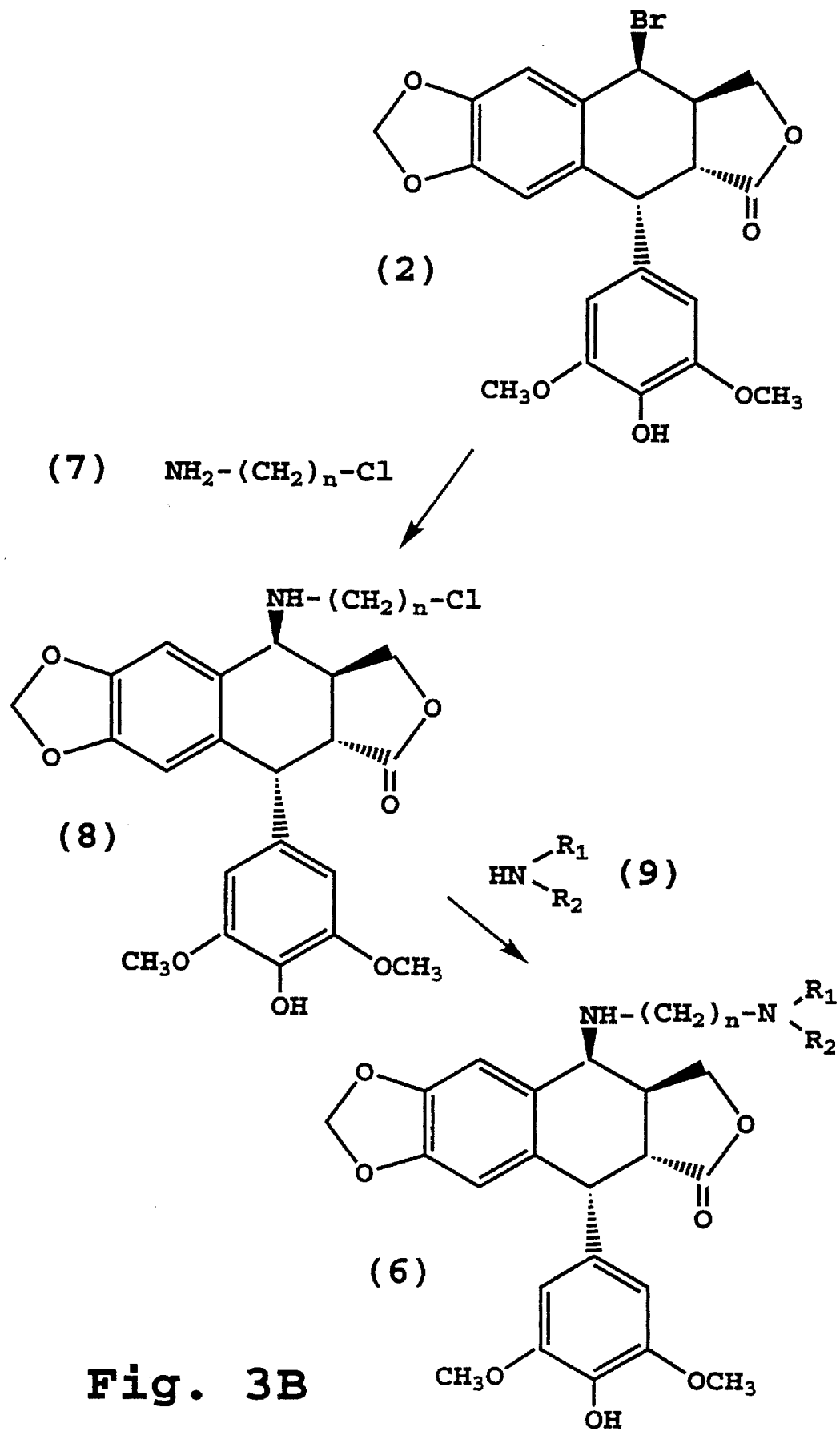
FIG. 3B shows steps in a second method of synthesis of 4β-aminoalkyl podophyllotoxin analog compounds of the type illustrated by compound 6.

The compounds can be formed, according to one general method by the reaction method illustrated in FIG. 3A, and detailed in Example 3. In this method, the 4'-O-Demethyl-4β-bromo-4-desoxypodophyllotoxin (compound 2) is combined with the appropriate $NH_2$—$(CH_2)_n$—$NR_1R_2$ (dialkylaminoalkyleneamine) (compound 5) in tetrahydrofuran, as detailed in Example 3. After reaction, the mixture is purified via column chromatography to give the desired compound 6.

Where the desired diakylaminealkylenediamine starting material is not commercially available, the method shown in FIG. 3B may be employed. Here compound 2 is reacted as above with an amino alkylchloride (compound 7), under conditions which favor derivatization of compound 2, to form the aminoalkylchloride podophyllotoxin compound 8. This compound is then reacted with a selected dialkyl amine (compound 9) to form the desired product (compound 6).

Figure 4A:
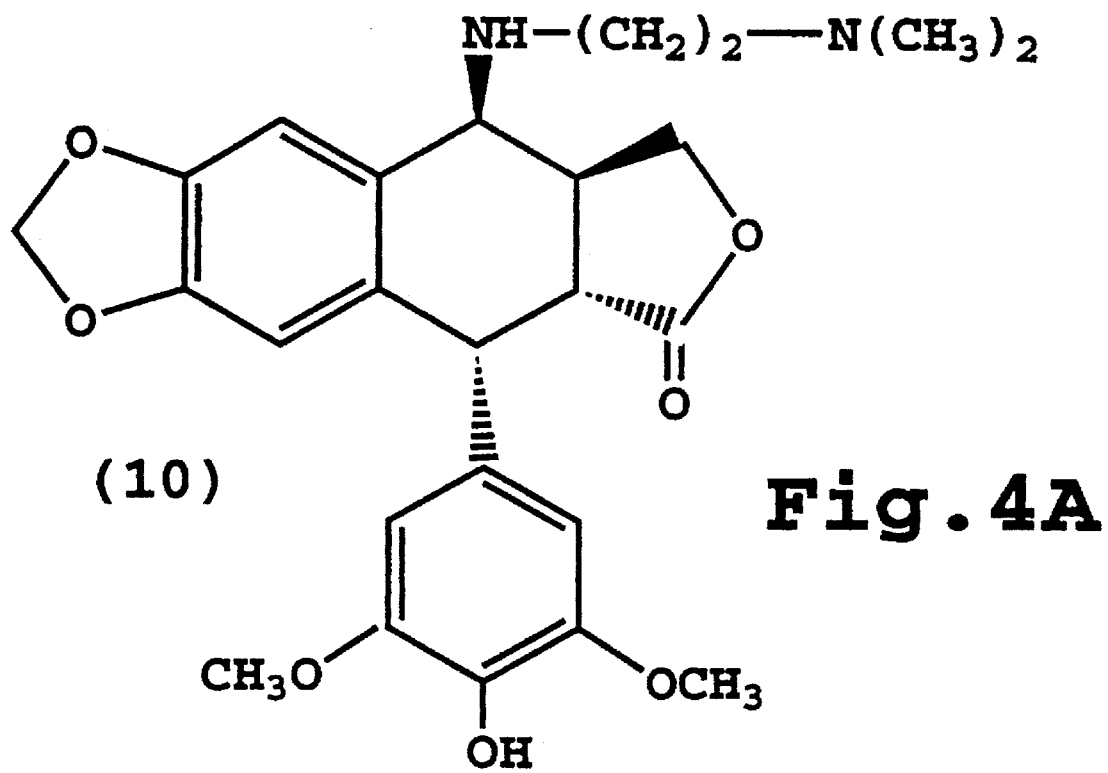
FIGS. 4A and 4B show structures of two aminoalkyl podophyllotoxin analog compounds 10 and 11, in accordance with a second general embodiment of the invention.
Figure 4B:
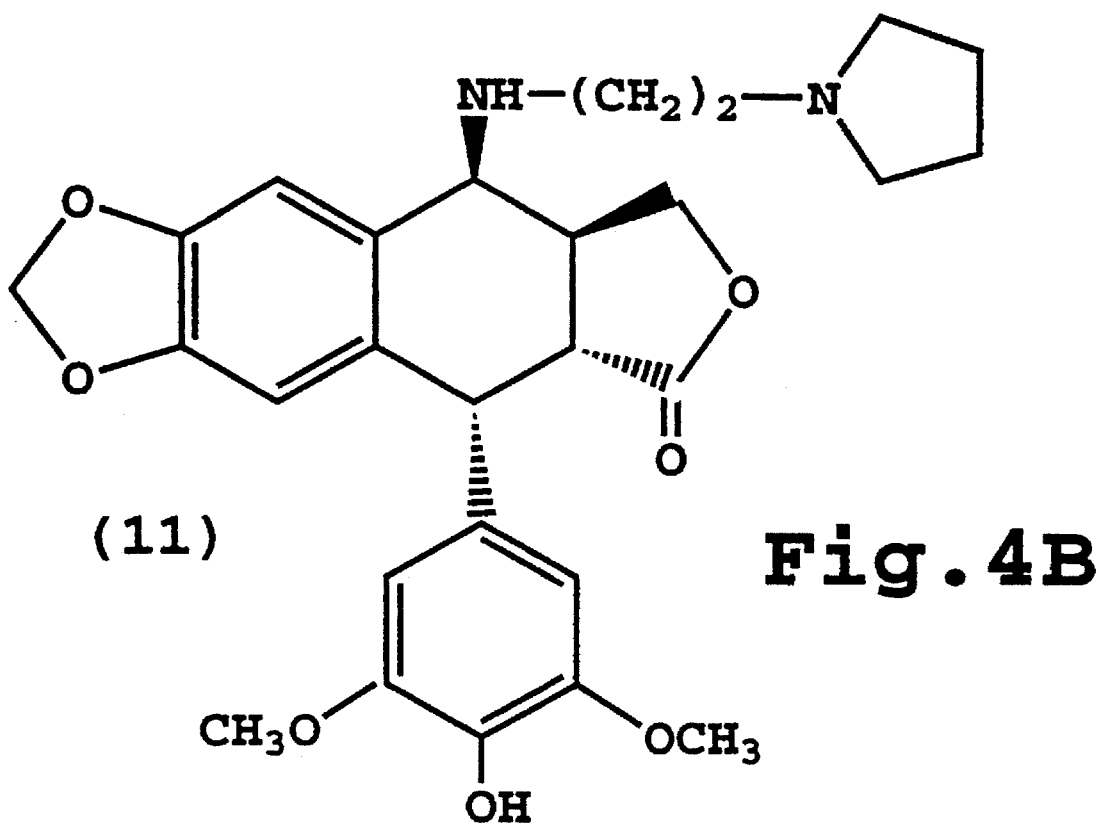

Exemplary analog compounds according to this embodiment of the invention are shown in FIGS. 4A and 4B. The dimethylethylenediamine analog shown in FIG. 4A (compound 10) is formed by reacting N,N dimethylethylenediamine with the compound 2, according to the FIG. 3 reaction scheme. The phrolidoneethylenediamine analog shown in FIG. 4B (compound 11) is likewise formed by reacting pyrrolidinethylamine with the compound 2.

As above, the ammonium salts of the dialkylalkylenediamine compounds in this class can be formed by reacting the compound with a stoichiometrical amount of an acid to form the corresponding water-soluble ammonium salt. Reaction conditions similar to those given in Example 7 are suitable, where the acid is selected, for example, from hydrochloride acid, hydrobromic acid, hydroiodic acid, sulfuric acid, phosphoric acid, nitric acid, acetic acid, propionic acid, formic acid, 1-ascorbic acid, tartaric acid, citric acid, lactic acid, maleic acid, fumaric acid, methanesulfonic acid, toluenesulfonic acid and benzenesulfonic acid.

It can be appreciated that the compounds of this embodiment can be easily synthesized to achieve a desired compound solubility in aqueous medium, by suitable choice of n, $R_1$, $R_2$, and amine charged salts. The water-solubility of the compounds can also be enhanced by reacting the compounds under alkylation conditions effective to form a charged, quaternary amine.

III. Dialkylamineanilino Podophyllotoxin Analog Compounds

The compounds in this embodiment have the general form for NH—R given below, where $R_1$ and $R_2$ are H or lower alkyl groups, as defined above.

NH—⟨benzene ring⟩—N(R$_1$)(R$_2$)

Figure 5A:
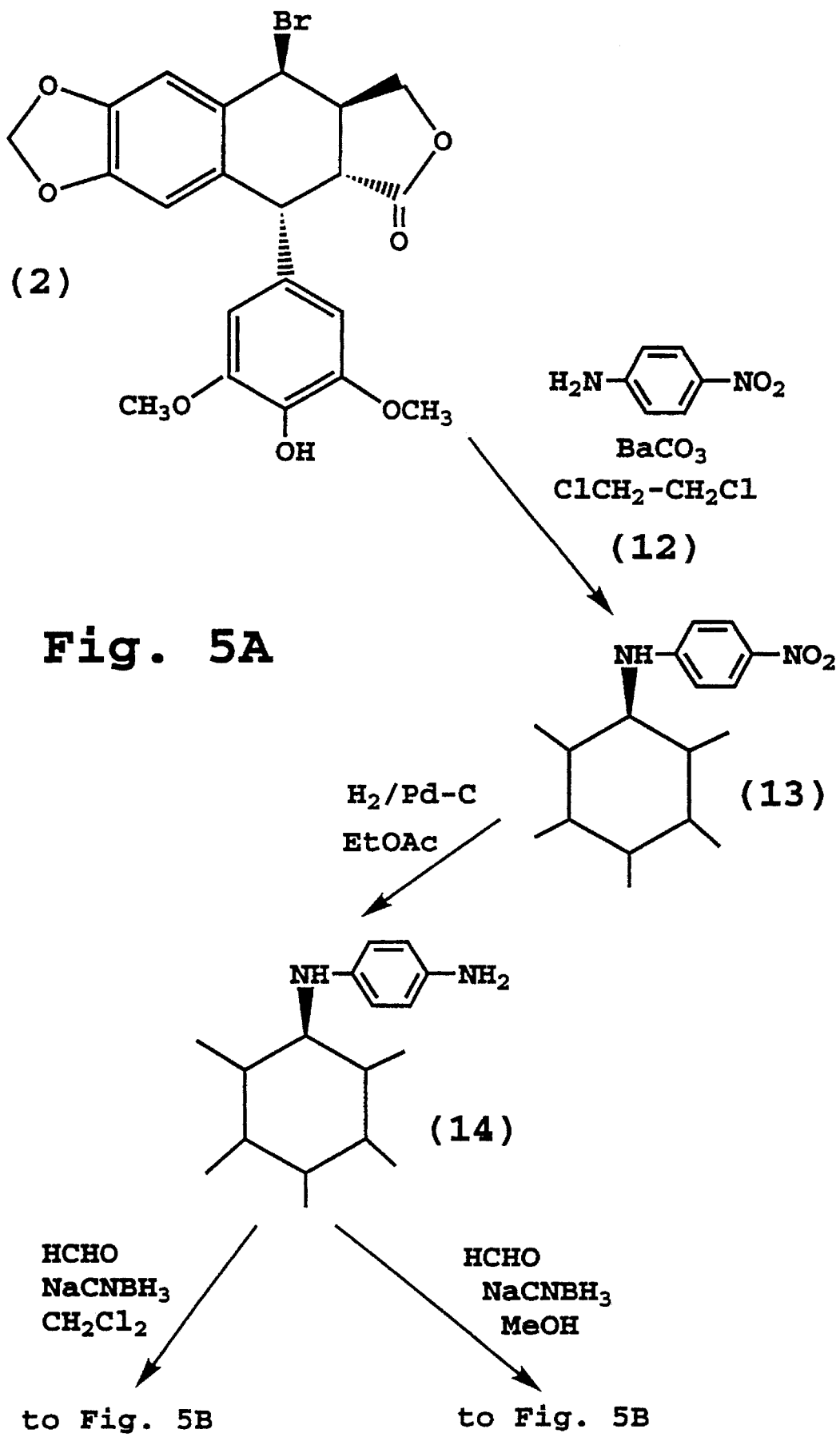
FIG. 5 shows steps in methods of synthesis of 4β-dialkylaminoanilino podophyllotoxin analog compounds, as exemplified by compounds 16 and 18, in accordance with a third general embodiment of the invention.
Figure 5B:
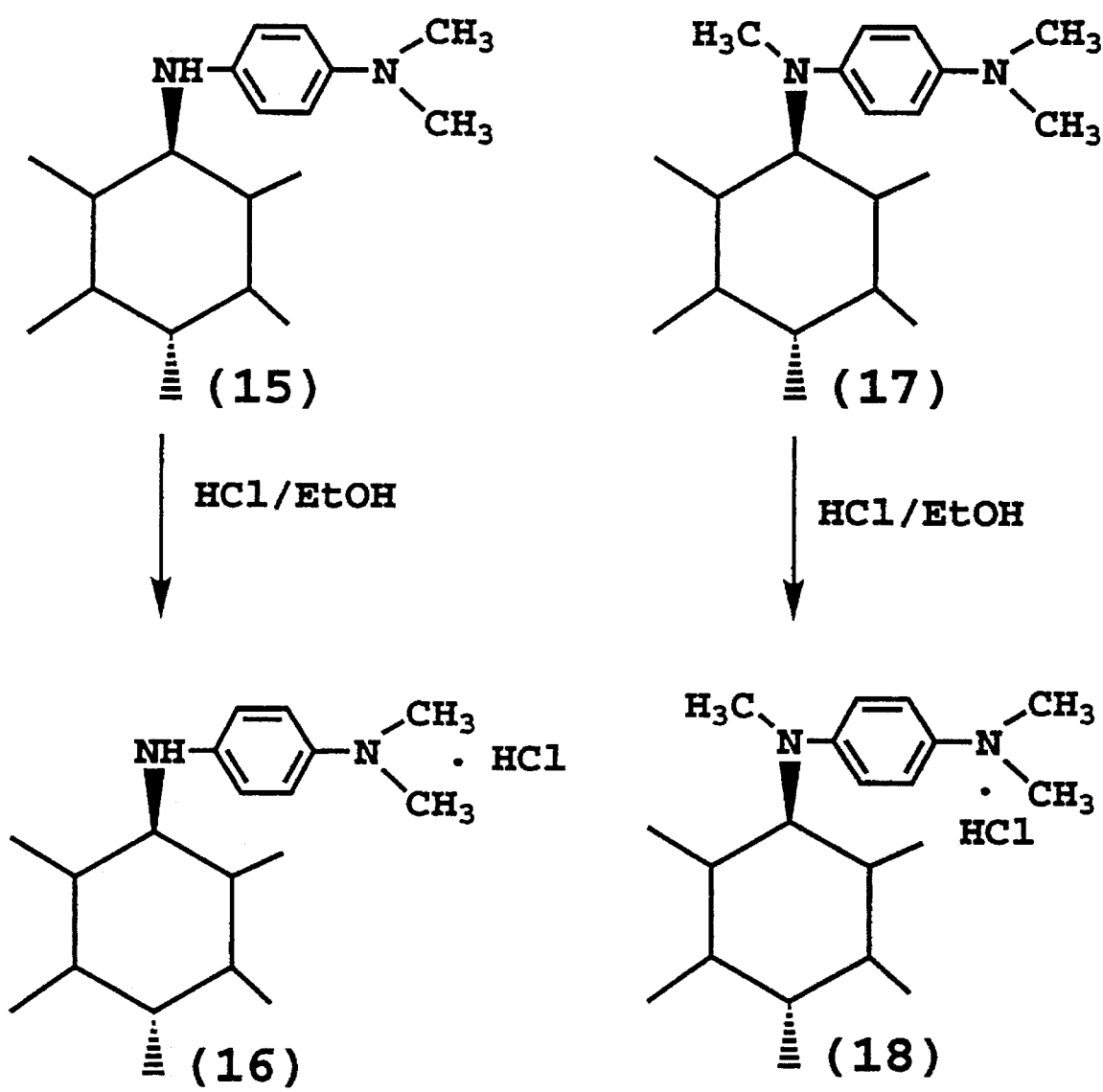

The compounds can be formed, according to one general method by the reaction method illustrated in FIG. 5, and detailed in Example 4. The first step in this method is the synthesis of the 4β-nitroanilino compound (compound 13 in FIG. 5) by reaction of the p-nitroaniline (compound 12) with the compound 2, as detailed in Example 4A. The nitro group is then reduced under hydrogen with a catalyst of palladium on activated carbon, as described in Example 4B.

The 4β-aminoanilino compound 14 can be converted to the desired dialkyl amine compound by one of two routes. In the first, the amine is reacted with formaldehyde in the presence of the reducing agent, $NaCNBH_3$ in dichloromethane, forming a predominantly dimethylaminoanilino analog (compound 15), as described in Example 4C. In the second route, compound 14 is reacted with formaldehyde in the presence of reducing agent $NaCNBH_4$ in methanol, forming more of dimethylamine-N-methylanilino compound 17. Details of this reaction are given in Example 4D. Both compounds 15 and 17 can be converted to corresponding HCl salts by reaction with HCl in ethanol, to give compounds 16 and 18, respectively, as detailed in Example 7. Other ammonium salts can be formed as described above.

Figure 6:
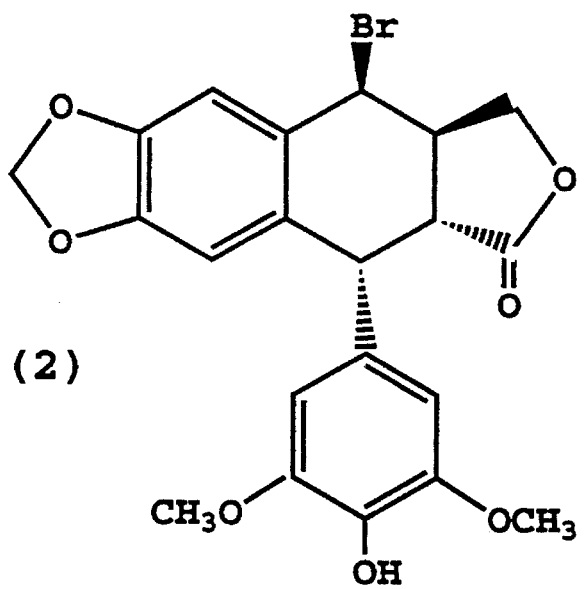
FIG. 6 shows an alternative method for preparing 4 β-dialkylaminoanilino podophyllotoxin analog compounds of the type shown in FIG. 5.
Figure 6:
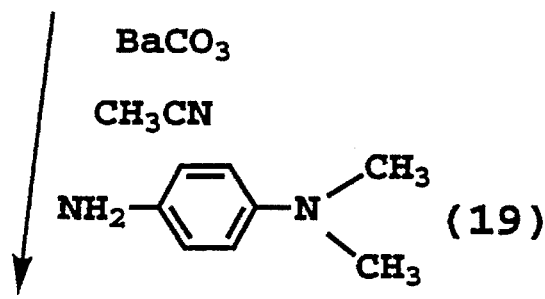
Figure 6:
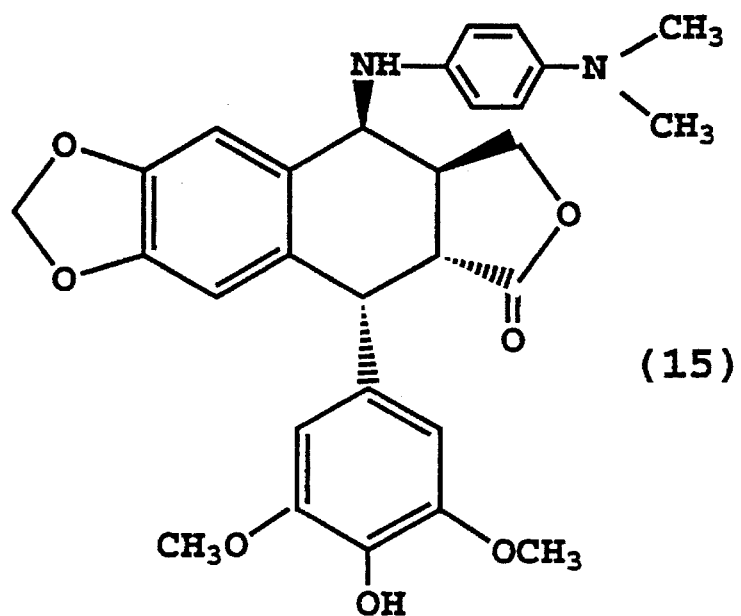

FIG. 6 illustrates a one step synthesis of dialkylaminonilino analog compounds. Here, the corresponding p-dialkylaminoaniline (compound 19) in acetonitrile is reacted under basic conditions with compound 2, to yield the desired analog compound 15 directly.

The following examples illustrate synthetic methods for preparing podophyllotoxin analogs in accordance with the invention. The examples are intended to illustrate, but in no way limit the scope of, the invention.

Materials

4'O-Demethylepipodophyllo-toxin, N,N-dimethylethylenediamine, podophyllotoxin, were obtained from Aldrich Chemical Co., or from other commercial sources.

Example 1

Synthesis of 4'-O-Demethyl-4β[anilino]-4-Desoxypodophyllotoxin Compounds

Synthesis of each of compounds 1–17 below was as follows.

A. Synthesis of 4'-O-Demethyl-4β-bromo-4-desoxypodophyllotoxin

A solution of 4'-O-Demethylepipodophyllotoxin (10 g, 24 mmol) (compound 1, FIG. 1) in 250 ml dry dicloromethane was kept at 0°, and dry hydrogen bromide was bubbled through the solution for 45 minutes, followed by bubbling of nitrogen to drive off excess HBr. The solution of compound 2 was evaporated under vacuum, and water was removed using benzene as an azeotropic mixture. The reaction converted compound 1 in FIG. 1 (4'-O-Demethylepipodophyllotoxin) to 11.5 g of 4'-O-Demethyl- 4β-bromo-4-desoxypodophyllotoxin compound 2, FIG. 1).

B. Synthesis of Aryl Amine Derivatives

A solution containing 4'-O-Demethyl-4β-bromo-4-desoxypodophyllotoxin (300 mg, 0.65 mmol), anhydrous barium carbonate (153 mg, 0.78 mmol), and the appropriate arylamine (0.78 mmol) in 7 mL of dry 1,2-dichloroethane under nitrogen was stirred overnight at room temperature. The reaction mixture was filtered, diluted with ethyl acetate, washed with water, dried over anhydrous magnesium sulfate, and purified via column chromatography (30 g silica gel with dichloromethane-acetone-ethyl acetate 100:5:5 or toluene-ethyl acetate 3:1 as an eluant). The 4'-O-Demethyl-4β-[anilino]-4-desoxypodophyllotoxin product (or related aryl compound) is shown at compound 4 in FIG. 1.

Compounds (4-a) to (4-q) formed by the above synthetic steps have the following characteristics.

4-a.

4'-O-Demethyl-4β-[2"-(ethoxycarbonyl)anilino]-4 -desoxypodophyllotoxin: yield 51%; crystals from ethanol; mp 231°–232° C.; $[\alpha]^{25}_D$ –102° C. (c=0.5, $CHCl_3$); IR (KBr) 3500 (OH), 3330 (NH), 2900 (aliphatic C—H), 1770 (lactone), 1670 (ester), 1600, 1580, 1500 and 1480 (aromatic C===C) $cm^{-1}$; $^1H$ NMR ($CDCl_3$) δ 8.00 (dd, J=1.6, 8.0 Hz, 1 H, 3'-H), 7.43 (t, J=8.0 Hz, 1 H, 4"-H), 6.77 (s, 1 H, 5-H), 6.71 (t, H, J=8.0 Hz, 5l-H), 6.64 (d, 1 H, J=8.0 Hz, 6"-H), 6.53 (s, 1 H, 8-H) 6.36 (s, 2 H, 2', 6'-H), 5.97 and 5.95 (AB q, J=1.3 Hz, 2 H, $OCH_2O$), 5.46 (s, 1 H, exchangeable, 4'-OH), 4.86 (d, J=4.2 Hz, 1 H, 4-H), 4.63 (d, J=4.9 Hz, 1 H, 1-H), 4.35 (t, J-7.3 Hz, 1 H, 11-H), 4.28 (q, 2 H, J=7.2 Hz, $CO_2CH_2CH_3$), 3.86 (t, J=7.3 Hz, 1 H, 11-H), 3.81 (s, 6 H, 3' 5'-$OCH_3$), 3.16 (dd, J=4.9, 14.1 Hz, 1 H, 2-H), 3.05 (m, 1 H, 3-H), 1.38 (t, J=7.2 Hz, 3 H, $CO_2CH_2CH_3$).

Anal. ($C_{30}H_{29}NO_9$) C, H, N.

4-b.

4'-O-Demethyl-4β-[3"-(methoxycarbonyl)anilino]-4-desoxypodophyllotoxin: yield 61%; crystals from methanol; mp 255°–258° C., $[\alpha]^{25}_D$ –98° (c=0.5, $CHCl_3$); IR (KBr) 3500 (OH), 3370 (NH), 2900 (aliphatic C—H), 1740 (lactone), 1700 (ester), 1600, 1500 and 1475 (aromatic C===C) $cm^{-1}$; $^1H$ NMR ($CDCl_3$) δ 7.45 (d, J=7.8 Hz, 1 H, 6"-H), 7.35 (t, J=7.8 Hz, 1 H, 5"-H), 7.22 (br, 1 H, 2"-H), 6.75 (br, 2 H, 5-H and 4"-H), 6.554 (s, 1H, 8-H), 6.33 (s, 2 H, 2', 6'-H, 5.97 and 5.95 (AB q, J=1.2 Hz, 2 H, $OCH_2O$), 5.45 (br, 1 H, exchangeable, 4'-OH), 4.76 (d, J=4.6 Hz, 1 H, 4-H), 4.51 (d, J=4.6 Hz, 1 H, 1-H), 4.40 (t, 1 H, 11-H), 3.96 (t, 1 H, 11-H), 3.91 (s, 3 H, $CO_2CH_3$), 3.81 (s, 6H , 3', 5'-$OCH_3$), 3.14 (dd, 1 H, 2-H), 3.05 (m, 1 H, 3-H).

Anal. ($C_{29}H_{27}NO_9$) C, H, N.

4-c.

4'-O-Demethyl-4β-[4"-(ethoxycarbonyl)anilino]-4 -desoxypodophyllotoxin: yield 48.7%; crystals from ethanol; mp 270°–271° C.; $[\alpha]^{25}_C$ –145° (c=0.33, $CHCl_3$), IR (KBr) 3500 (OH), 3370 (NH), 2940 (aliphatic C—H), 1762 (lactone), 1695 (ester), 1610, 1520 and 1480 (aromatic C===C) $cm^{-1}$; $^1H$ NMR ($CDCl_3$) δ 7.92 (d, J=8.8 Hz, 2 H, 3", 5"-H), 6.77 (s, 1 H, 5-H), 6.55 (d, J=8.8 Hz, 2 H, 2", 6"-H), 6.54 (s, 1 H, 8-H), 6.33 (s, 2 H, 2", 6"-H), 5.99 and 5.97 (AB q, J=1.1 Hz, 2 H, $OCH_2O$), 5.44 (s, 1 H, exchangeable, 4'-OH), 4.78 (d, J=3.3 Hz, 1 H, 4-H), 4.62 d, J=4.5 Hz, 1 H, 1-H), 4.40 (t, J=7.5 Hz, 1 H, 11-H), 4.37 (q, J=7.1 Hz, 2 H, $CO_2CH_2CH_3$), 4.32 (m, 1 H, exchangeable, NH) 3.92 (t, J=7.5 Hz, 1 H, 11-H), 3.80 (s, 6 H, 3',5'-$OCH_3$), 3.10 (dd, 1 H, 2-H), 3.08 (m, 1 H, 3-H), 1.38 (t, J=7.1 Hz, 3 H, $CO_2CH_2CH_3$).

Anal. ($C_{30}H_{29}NO_9$) C, H, N.

4-d.

4-O-Demethyl-4β-[3"-(methoxycarbonyl-4"-hydroxyanilino]-4-desoxypodophyllotoxin: yield 49%; crystals from ethanol; mp 158°–160° C.; $[\alpha]^{25}_D$ –115° (c=0.5, $CHCl_3$); IR (KBr) 3500 (OH), 3370 (NH), 2980 (aliphatic C—H), 1760 (lactone), 1660 (ester), 1600, 1500 and 1470 (aromatic C===C) $cm^{-1}$; $^1H$ NMR ($CDCl_3$) δ 7.25 (br, 1 H, 2"-H) 6.94 (d, J=8.0 Hz, 1 H, 5l-H), 6.91 (s, 1 H, 4"-OH), 6.89 (s, 1 H, 5-H), 6.74 (dd, J=1.1, 8.0 Hz, 6"-H), 6.72 (s, 1 H, 8-H), 6.53 (s, 2H, 2'6'-H), 5.98 and 5.96 (AB q, J=1.1 Hz, 2 H, $OCH_2O$), 5.43 (s, 1 H, 4'-H), 4.61 (m, 2 H, 4-H and 1-H), 4.39 (t, J=7.3 Hz, 1 H, 11-H), 4.10 (t, J–7.3 Hz, 1 H, 11-H), 3.95 (s, 2 H, 3"-$CO_2CH_3$), 3.80 (s, 6 H, 3', 5'-$OCH_3$), 3.18 (dd, 1 H, 2-H), 3.11 (m, 1 H, 3-H).

Anal. ($C_{29}H_{27}NO_{10}$).

4-e.

4'-O-Demethyl-4β-[3"-hydroxy-4"-(methoxycarbonyl)-anilino]-4-desoxypodophyllotoxin: yield 45%; crystals from ethanol; mp 177°–180° C.; $[\alpha]^{25}_D$ –146° (c=.05, $CHCl_3$); IR (KBr) 3500 (OH), 3360 (NH), 2900 (aliphatic C—H), 1750 (lactone), 1650 (ester), 1620, 1520 and 1480 (aromatic C===C) $cm^{-1}$; $^1H$ NMR ($CDCl_3$) δ 7.65 (d, J=8.5 Hz, 1 H, 5l-H), 6.76 (s, 1 H, 5-H), 6.54 (s, 1 H, 8-H), 6.32 (s, 2 H, 2', 6'-H), 6.06 (dd, J=1.2, 8.5 Hz, 1 H, 6"-H), 6.04 (d, J=1.2 Hz, 1 H, 2"-H), 5.99 (s, 1 H, $OCH_2O$), 5.97 (s, 1 H, $OCH_2O$), 5.43 (s, 1 H, 4"-OH), 4.72 (m, 1 H, NH), 4.61 (d, J=4.3 Hz, 1 H, 4-H), 4.41 (dd, 1 H, 11-H), 4.30 (d, J=4.0 Hz, 1 H, 1-H), 3.92 (t, 1 H, 11-H), 3.90 (s, 3 $H_2CH_3$), 3.79 (s, 6 H, 3", 5"-$OCH_3$), 3.05 (m, 2 H, 2-H and 3-H).

Anal. ($C_{29}H_{27}NO_{10}$).

4-f.

4'-O-Demethyl-4β-[3",5"-bis(methoxycarbonyl)anilino]-4-desoxypodophyllotoxin: yield 35%; crystals from ethanol; mp 170°–173° C. dec; $[\alpha]^{25}_D$ –111° (c=0.5, $CHCl_3$); IR (KBr) 3500 (OH), 3380 (NH), 2900 (aliphatic C—H), 1780 (lactone), 1720 (ester), 1605, 1510 and 1485 (aromatic C===C) $cm^{-1}$; $^1H$ NMR ($CDCl_3$) δ 8.08 (br, 1 H, 4"-H), 7.42 (br, 2 H, 2", 6"-H), 6.72 (s, 1 H, 5-H), 6.55 (s, 1 H, 8-H), 6.34 (s, 2 H, 2", 6"-H), 5.99 (s, 1 H, $OCH_2O$), 5.97 (s, 1 H, $OCH_2O$), 5.45 (s, 1 H, 4'-OH), 4.80 (m, 1 H, NH), 4.63 (d, J=4.4 Hz, 1 H, 4-H), 4.45 (t, 1 H, 11-H), 4.17 (d, J=5.5 Hz, 1 H, 1 -H), 3.94 (s, 6 H, 3", 5"-$CO_2CH_3$), 3.90 (t, 1 H, 11-H), 3.81 (s, 6 H, 3', 5'-$OCH_3$), 3.10 (m, 2 H, 2-H and 3-H).

Anal. $C_{31}H_{29}NO_{11}$.$H_2O$) C, H, N.

4-g.

4'-O-Demethyl-4β-[3"-(methoxyanilino]-4-desoxypodophyllotoxin: yield 57%; $[\alpha]^{25}_D$ –117° (c=0.5, $CHCl_3$); crystals from ethyl acetate; mp 277°–279° C.; IR (KBr) 3360 (NH), 2900 (aliphatic C—H), 1740 (lactone), 1600, 1500 and 1470 (aromatic C===C) $cm^{-1}$; $^1H$ NMR ($CDCl_3$) δ 7.11 (t, J=8.2 Hz, 1 H, 5"-H), 6.78 (s, 1 H, 5-H), 6.53 (s, 1 H, 8-H). 6.35 (dd, J=1.7, 8.2 Hz, 1 H, 4"-H), 6.33 (s, 2 H, 2', 6'-H), 6.10 (dd, J=1.7, 8.2 Hz, 1 H, 6"-H), 6.10 (t, J=1.7 Hz, 1 H, 2"-H), 5.97 and 5.95 (AB q, J=0.7 Hz, 2 H, $OCH_2O$), 5.43 (s, 1 H, 4'-OH), 4.68 (d, 1 H, 4-H), 4.59 (d, J=4.8 Hz, 1 H, 1-H), 4.30 (t, 1 H, 11-H), 4.01 (t, 1 H, 11-H), 3.84 (m, 1 H, NH), 3.79 (s, 6 H, 3', 5'-OCH₃), 3.78 s, 3 H, 3"-OCH₃), 3.13 (dd, 1 H, 2-H), 2.99 (m, 1 H, 3-H).

Anal. C₂₈H₂₇NO₈) C, H, N.

4-h.

4'-O-Demethyl-4β-(3"-acetylanilino)-4 -desoxypodophyllotoxin: yield 42%; crystals from ethyl acetate-ether; mp 259°–262° C.; [α]²⁵_D –121° (c=0.5, CHCl₃); IR (KBr) 3380 (NH), 2900 (aliphatic C—H), 1738 (lactone), 1660 (ester), 1590, 1575 and 1500 (aromatic C═══C) cm⁻¹; ¹H NMR (CDCl₃) δ 7.34 (m, 2 H, 5l-H and 6"-H), 7.16 (br, 1 H, 2"-H), 6.75 (dd, J=1.8, 8.0 Hz, 1 H, 4"-H), 6.75 (s, 1 H, 5-H), 6.54 (s, 1 H, 8-H), 6.33 (s, 2 H, 2', 6'-H), 5.98 and 5.96 (AB q, J=1.2, 2 H, OCH₂O), 5.45 (s, 1 H, 4'-OH), 4.79 (m, 1 H, NH), 4.61 (d, J=4.9 Hz, 1 H, 4-H), 4.42 (t, 1 H, 11-H), 4.02 (d, J=4.9 Hz, 1 H, 1-H), 3.92 (t, 1 H, 11-H), 3.81 (s, 6 H, 3', 5'-OCH₃), 3.12 (dd, J=4.9, 14.0 Hz, 1 H, 2-H, 3.04 (m, 1 H, 3-H).

Anal. (C₂₉H₂₇NO₈) C, H, N.

4-i.

4'-O-Demethyl-4β-[3"-(hydroxymethyl)anilino]-4 -desoxypodophyllotoxin: yield 43%; crystals from ether-hexane; mp 189°–192° C.; [α]²⁵_D –110° (c=0.5, CHCl₃); IR (KBr) 3500 (OH), 3380 (NH), 2890 (aliphatic C—H), 1745 (lactone), 1595, 1500 and 1470 (aromatic C═══C) cm⁻¹; ¹H NMR (CDCl₃) δ 7.20 (t, J=8.1 Hz, 1 H, 5"-H), 6.78 (d, 2 H, 5-H and 4"-H), 6.62 (br, 1 H, 2"-H), 653 (s, 1 H, 8-H), 6.48 (dd, J=1.8, 8.1 Hz, 1 H, 6"-H), 6.34 (s, 2 H, 2', 6'-H), 5.97 and 5.95 (AB q, J=0.9 Hz, 4 H, OCH₂O), 5.45 (s, 1 H, 4'-OH), 4.71 (d, J=3.4 Hz, 1H, 4-H), 4.65 (s, 2 H, 3"-CH₂OH), 4.60 (d, J=4.9 Hz, 1 H, 1-H), t, 1 H, 11-H), 3.99 (t, 1 H, 11-H), 3.80 (s, 6 H, 3', 5'-OCH₃), 3.77 (m, 1 H, NH), 3.15 (dd, J=4.9, 14.0 Hz, 1 H, 2-H), 3.00 (m, 1 H, 3-H).

Anal. (C₂₈H₂₇NO₈) C, H, N.

4-j.

4'-O-Demethyl-4β-(3",4",5"-trimethoxyanilino)-4 -desoxypodophyllotoxin: yield 60%; crystals from ethanol-ether; mp 240°–242 ° C.; [α]²⁵_D –110° (c=0.5, CHCl₃); IR (KBr) 3500 (OH), 3460 (NH), 2930 (aliphatic C—H), 1765 (lactone), 1600, 1500, 1476 (aromatic C═══C) cm⁻¹; ¹H NMR (CDCl₃) δ 6.80 (s, 1 H, 5-H), 6.53 (s, 1 H, 8-H), 6.34 (s, 2 H, 2', 6'-H, 5.98 and 5.96 (AB q, J=1.2 Hz, 2 H, OCH₂O), 5.77 (s, 2 H, 2", 6"-H), 5.45 (br, 1 H, 4'-OH), 4.62 (m, 2 H, 4-H and 1-H), 4.35 (t, 1 H, 11-H), 4.08 (t, 1 H, 11-H), 3.81 (s, 9 H, 3", 4", 5"-OCH₃), 3.80 (s, 6 H, 3', 5'-OCH₃), 3.18 (dd, 1 H, 2-H), 3.00 (m, 1 H, 3-H).

Anal. (C₃₀H₃₁NO₁₀·½H₂O) C, H, N.

4-k.

4'-O-Demethyl-4β-(3"-nitroanilino)-4 -desoxypodophyllotoxin: yield 47%; crystals from ethanol; mp 185°–187° C.; [α]²⁵_d –96° (c=0.5, CHCl₃); IR (KBr) 3390 (NH), 2900 (aliphatic C—H), 1750 (lactone), 1520 and 1345 (NO₂) cm⁻¹, ¹H NMR (CDCl₃) δ 7.63 d, J=8.8 Hz, 1 H, 4"-H), 7.38 (m, 2 H, 2", 5"-H), 6.85 (d, J=8.8 Hz, 1 H, 6"-H), 6.75 (s, 1 H, 5-H), 6.56 (s, 1 H, 8-H), 6.33 (s, 2 H, 2', 6'-H), 6.00 (s, 1 H, OCH₂O), 5.98 (s, 1 H, OCH₂O), 5.45 (s, 1 H, 4'-OH), 4.78 (m, 1 H, NH), 4.62 (d, J=3.2 Hz, 4-H), 4.55 (t, 1 H, 11-H), 4.25 (d, 1 H, 1-H), 3.93 (t, 1 H, 11 -H), 3.81 (s, 6 H, 3', 5'-OCH₃), 3.11 (m, 2 H, 2-H and 3-H).

Anal. (C₂₇H₂₄N₂O₉) C, H, N.

4-l.

4'-O-Demethyl-4β-(4"-nitroanilino)-4 -desoxypodophyllotoxin: yield 44%; crystals from ethyl acetate; mp 205°–207° C.; [α]²⁵_D –170° (c=0.5, CHCl₃); IR (KBr) 3500 (OH), 3470 (NH), 2920 (aliphatic C—H), 1775 (lactone), 1600, 1520 and 1490 aromatic C═══C), 1330 and 1310 (NO₂) cm⁻¹; ¹H NMR (CDCl₃) δ 8.15 (d, J=9.1 Hz, 2 H, 3", 5"-H), 6.67 (s, 1 H, 5-H), 6.60 (d, 3 H, 8-H and 2", 6"-H), 6.32 (s, 2 H, 2", 6"-H), 6.00 (s, 1 H, OCH₂O), 5.98 (s, 1 H, OCH₂O), 5,46 (s, 1 H, 4"-OH), 4.83 (m, 1 H, NH), 4.62 (m, 2 H, 4-H and 1-H), 4.41 (t, 1 H, 11-H), 3.90 (t, 1 H, 11-H), 3.80 (s, 6 H, 3", 5"-OCH₃), 3.10 (m, 2 H, 2-H and 3-H).

Anal (C₂₇H₂₄N₂O₉) C, H, N.

4-m.

4-O-Demethyl-4β-(2"-hydroxy-5"-nitroanilino)-4 -desoxypodophyllotoxin: yields 35%; crystals from ethanol; mp 192°–194° C. dec; [α]²⁵_D –114° (c=0.5, CHCl₃); IR (KBr) 3540 (OH), 3420 (NH), 2925 (aliphatic C—H), 1775 (lactone), 1630 and 1600 (aromatic C═══C), 1530 and 1350 (NO₂) cm⁻¹, ¹H NMR (CDCl₃) δ 7.62 (dd, J=2.6, 8.6 Hz, 4"-H), 7.38 (d, J=2.6, 1 H, 6"-H), 6.80 (D, J=8.6 Hz, 1 H, 3"-H) 6.34 (s, 1 H, 5-H), 6.29 (s, 1 H, 8-H), 6.19 (s, 2 H, 2', 6'-H), 6.00 and 5.98 (AB q, J= 1.2 Hz, 2 H, OCH₂O), 5.50 (s, 1 H, 4'-OH), 4.78 (m, 1 H, NH), 4.63 (d, J=4.6 Hz, 1 H, 4-H), 4.58 (d, J=6.1 Hz, 1 H, 1-H), 4.23 (t, 1 H, 11-H), 3.92 (t, 1 H, 11-H), 3.81 (s, 6 H, 3', 5'-OCH₃), 3.17 (m, 2 H, 2-H and 3-H).

Anal. (C₂₇H₂₄N₂O₁₀·½H₂O) C, H, N.

4-n.

4-O-Demethyl-4β-[",5"-bis(trifluoromethyl)anilino]-4 -desoxypodophyllotoxin: yield 59%; crystals from ether-hexane; mp 165°–168° C.; [α]²⁵_D –85° (c=0.5, CHCl₃); IR (KBr) 3500 (OH), 3360 (NH), 2930 (aliphatic C—H), 1780 (lactone), 1620, 1510 and 1485 (aromatic C═══C) cm⁻¹; ¹H NMR (CDCl₃) δ 7.02 (br, 1 H, 4"-H), 6.93 (br, 2 H, 2", 6"-H), 6.78 (s, 1 H, 5-H), 6.57 (s, 1 H, 8-H), 6.33 (s, 2 H, 2', 6'-H), 6.01 and 5.99 (AB q, J=1.1 Hz, 2 H, OCH₂O), 5.45 (s, 1 H, 4'-OH), 4.76 (m, 1 H, NH), 4.63 (d, J=3.5 Hz, 1 H, 4-H), 4.39 (m, 1 H, 11-H), 4.33 (d, J=5.8 Hz, 1 H, 1-H), 3.88 (m, 1 H, 11-H), 3.80 (s, 6 H, 3', 5'-OCH₃), 3.09 (m, 2 H, 2-H and 3-H).

Anal. (C₂₉H₂₃F₆NO₇) C, H, N.

4-o.

4'-O-Demethyl-4β-(2"-pyridylamino)-4 -desoxypodophyllotoxin: yield 26.6%; crystals from ethanol; mp 215°–218° C. dec; [α]²⁵_D –82° (c=0.33, CHCl₃); IR (KBr), 3500 (OH), 3360 (NH), 2950 (aliphatic C—H), 1760 (lactone), 1690, 1645, 1600 and 1460 (aromatic ring) cm⁻¹; ¹H NMR (CDCl₃) δ 8.11 (d, 1 H, 6"-H), 7.45 (m, 1 H, 4"-H), 6.81 (s, 1 H, 5-H), 6.67 (m, 1 H, 5"-H), 6.55 (s, 1 H, 8-H), 6.45 (d, 1 H, 3"-H), 6.34 (s, 2 H, 2", 6"-H), 5.98 and 5.96 (AB q, J=1.3 Hz, 2 H, OCH₂O), 5.34 (br, 1 H, exchangeable, 4'-OH), 5.35 (m, 1 H, exchangeable, NH), 4.60 (d, J=4.2 Hz, 1 H, 4-H), 4.24 (m, 2 H, 1-H and 11-H), 3.85 (m, 1 H, 11 -H), 3.78 (s, 6 H, 3', 5'-OCH₃), 3.05 (m, 2-H, 2-H and 3-H).

Anal. (C₂₆H₂₄N₂O₇·½H₂O) C, H, N.

4-p.

4-O-Demethyl-4β-(3"-pyridylamino)-4 -desoxypodophyllotoxin: yield 10%. crystals from ethanol; mp 179°–181° C. dec; [α]²⁵_D –99° (c=0.33, CHCl₃); IR (KBr) 3500 (OH), 3350 (NH), 2900 (aliphatic C—H), 1765 (lactone), 1575, 1500 and 1470 (aromatic ring) cm⁻¹; ¹H NMR (CDCl₃) δ 8.08 (d, J=5.5 Hz, 1 H, 6"-H), 8.02 (br, 1 H, 2"-H), 7.16 (m, 1 H, 5"-H), 6.85 (dd, 1 H, 4"-H), 6.75 (s, 1 H, 5-H), 6.55 (s, 1 H, 8-H), 6.32 (s, 2 H, 2', 6'-H), 5.99 and 5.97 (AB q, J=1.3 Hz, 2 H, OCH₂O), 4.65 (d, J=4.9 Hz, 1 H, 4-H), 4.60 (m, 1 H, 1-H), 4.20 (t, J=8.2 Hz, 1 H, 11-H), 3.90 (m, 2 H, 11-H and NH), 3.80 (s, 6 H, 3',5'-OCH₃), 3.18 (dd, J=4.9, 14.1 Hz, 1 H, 2-H), 3.03 (m, 1 H, 3-H).

Anal. (C₂₆H₂₄N₂O₇·½H₂O) C, H, N.

4-q.

4'-O-Demethyl-4β-(3"-quinolylamino)-4 -desoxypodophyllotoxin: yield 49.4%; crystals from ethanol-ether; mp 243°–246° C. dec [α]²⁵_D –179° (c=0.5, CHCl₃); IR (KBr), 3460 (OH), 3380 (NH), 2900 (aliphatic C—H), 1775 (lactone), 1605, 1510 and 1480 (aromatic ring) cm$^{-1}$; $^1$H NMR (CDCl$_3$) δ 8.46 (d, J=2.9 Hz, 2"-H), 7.97 (m, 1 H, 4"-H), 7.65 (m, 1 H, 7"-H), 7.48 (m, 2 H, 5", 6"-H), 6.99 (d, J=2.9 Hz, 8"-H), 6.76 (s, 1 H, 5-H), 6.57 (s, 1 H, 8-H), 6.35 (s, 2 H, 2', 6'-H), 6.00 and 5.98 (AB q, J=1.1. Hz, 2H, OCH$_2$O), 5.48 (s, 1 H, exchangeable, 4'-OH, 4.78 (d, J=3.5 Hz, 1 H, 4-H), 4.64 (d, J=4.8 Hz, 1 H, 1-H), 4.45 (t, 1 H, 11-H), 4.23 (d, 1 H, exchangeable, NH), 3.99 (t, 1 H, 11-H), 3.81 (s, 6 H, 3', 5'-OCH$_3$), 3.15 (m, 2 H, 2-H and 3 -H).

Anal. (C$_{30}$H$_{26}$N$_2$O$_7$) C, H, N.

Example 2

Synthesis of 4"-O-Demethyl-4β[anilino]-4 -Desoxypodophyllotoxin chloride salts Compounds (4-r)–(4-t) were prepared as follows: A solution of compounds 4-k, 4-l, or 4-m from Example 1 (140 mg) in ethyl acetate (10 mL) was adjusted with 1 N hydrogen chloride solution in methanol to pH=1–2. After 10% palladium on activated carbon (70 mg) was added, the solution was stirred under hydrogen for 3 h. The catalyst was filtered off and washed with methanol. The filtrate and washings were combined and evaporated to give a solid. The solid was washed with ether five times to drive the free hydrogen chloride away, followed by crystallization from methanol-ether to afford 4-r, 4-s, and 4-t, respectively.

4-r.

4'-O-Demethyl-4β-(3"-aminoanilino)-4 -desoxypodophyllotoxin hydrochloride: yield 75%; mp 203°–206 ° C. dec; [α]$^{25}_D$–108° (c=0.5, CH$_3$OH); IR (KBr) 3450, 3360 and 3000 (NH$_3^+$ and OH), 2900 (aliphatic C—H), 1765 (lactone), 1605, 1510, 1500 and 1475 cm$^{-1}$; $^1$H NMR (CD$_3$OD) δ 6.89 (t, J=7.8 Hz, 1 H, 5"-H), 6.76 (s, 1 H, 5-H), 6.48 (s, 1 H, 8 -H), 6.35 (s, 2 H, 2', 6'-H), 6.08 (m, 3 H, 2", 4" and 6"-H), 5.92 (s, 2 H, OCH$_2$O), 4.76 (d, J=4.2 Hz, 1 H, 4-H), 4.56 (d, J=5.0 Hz, 1 H, 1-H), 4.39 (t, J=7.9 Hz, 1 H, 11-H), 3.95 (t, J=7.9 Hz, 1 H, 11-H), 3.73 (s, 6H, 3', 5'-OCH$_3$).

Anal. (C$_{27}$H$_{27}$N$_2$ClO$_7$) C, H.

4-s.

4'-O-Demethyl-4β2-(4"-aminoanilino)-4 -desoxypodophyllotoxin hydrochloride: yield 72%; mp 187°–190 ° C. dec; [α]$^{25}_D$–100° (CH$_3$OH); IR (KBr) 3420, 2920 and 2600 (NH$_3^+$OH and aliphatic C—H), 1770 (lactone), 1620, 1520 and 1490 cm$^{-1}$; $^1$H NMR (DMSO-d$_6$) δ 9.90 (br, NH$_3^+$, exchangeable), 7.12 (d, J=8.6 Hz, 2 H, 2", 6"-H), 6.55 (t, 3 H, 3", 5"-H and 5-H), 6.38 (br, 1"-NH, exchangeable), 6.23 (s, 2 H, 2', 6'-H), 6.01 (s, 1 H, OCH$_2$O), 5.95 (s, 1 H, OCH$_2$O), 4.85 (br, 1 H, 4-H), 4.50 (d, J=4.9 Hz, 1 H, 1-H), 4.35 (t, J=7.6 Hz, 1 H, 11-H), 3.65 (br, 7 H, 11-H and 3', 5'-OCH$_3$), 3.28 (dd, J=4.9, 14.1 Hz, 1 H, 2-H), 3.00 (br, 1 H, 3-H).

Anal. (C$_{27}$H$_{27}$N$_2$Cl$_2$O$_7$·H$_2$O) C, H.

4-t.

4'-O-Demethyl-4β-(2"-hydroxy-5"-aminoanilino)-4 -desoxypodophyllotoxin hydrochloride: yield 82%; mp>300 ® C.; IR (KBr) 3350 (NH$_3^+$ and OH), 1760 (lactone), 1600 and 1500 cm$^{-1}$; $^1$H NMR δ (CH$_3$OD) 6.76 (d, J=8.2 Hz, 1 H, 3"-H), 6.72 (s, 1 H, 5-H), 6.58 (d, J=1.9 Hz, 1 H, 6"-H), 6.00 (s, 1 H, 8-H), 6.49 (dd, J=1.9 Hz, 8.2 Hz, 1 H, 4"-H), 6.26 (s, 2 H, 2', 6'-H), 6.00 (s, 1 H, OCH$_2$O), 5.97 (s, 1 H, OCH$_2$O), 5.10 (d, 1 H, 4-H), 4.75 (br, 1 H, 1-H), 4.45 (m, 2 H, 11-H), 3.65 (s, 6 H, 3', 5%$0 -OCH$_3$), 3.45 (dd, 1 H, 2-H), 3.00 (m, 1 H, 3-H).

Anal. (C$_{27}$H$_{27}$ClN$_2$O$_8$) C, H, N.

Example 3

Synthesis of 4-O-Demethyl-4β-[3"-(N,N-dimethyl)-ethylenediamino-4-desoxypodophyllotoxin 4"-O-Demethyl-4β-bromo-4-desoxypodophyllotoxin (compound 2 in FIG. 3A) was prepared as in Example 1. Dry tetrahydrofuran (20 ml) was added to 1 g of compound 2, and the suspension was heated to reflux under nitrogen. N, N-dimethylethylenediamine (95%, 0.5 ml) was injected into the suspension, and the reaction mixture was refluxed for 6 hours, then evaporated under vacuum. The desired 4"-O-Demethyl- 4β-[3"-(N,N-dimethyl)-ethylenediamino-4 -desoxypodophyllotoxin (FIG. 4A) was obtained (140 mg) through flash silica gel chromatography using mixed ethylacetate and hexane (3:1 to 1:1) as the eluent and recrystallization in acetone. Yield: 13.8%.

The compound is characterized by: mp 178°–180° C.; IR (KBr) 3350 (NH), 2940 (aliphatic C—H), 1765 (lactone), 1610, 1520, 1510, and 1475 cm$^{-1}$, $^1$H NMR (CDCl$_3$) δ 6.78 (s, 1 H, 5-H), 6.47 (s, 1 H, 8-H), 6.28 (s, 2 H, 2",6"-H), 5.96 (s, 1 H, OCH$_2$O), 4.51 (d, J=5Hz, 1 H, 1-H), 4.35 (m, 2 H, 11-H), 3.82 (d, J=4Hz, 1 H, 4-H), 3.77 (s, 6 H, 3',5'-OCH$_3$), 3.33 (dd, J=5, 14Hz, 1 H, 2-H), 2.91 (m, 1 H, 1"-H), 2.78 (m, 1 H, 3-H), 2.65 (m, 1 H, 1"-H), 2.45 (m, 2 H, 2"-H), 2.25 (s, 6 H, N(CH$_3$)$_2$).

Anal. C$_{25}$H$_{30}$O$_7$N$_2$) C, H, N.

Example 4

Synthesis of 4'-O-Demethyl-4β-[4"-dimethylaminoanilino]-4-desoxypodophyllotoxin: Method 1

A. Synthesis of 4'-O-Demethyl-4β-[4"-nitroanilino]-4 -desoxypodophyllotoxin (compound 13)

A solution containing compound 2 in FIG. 5 (300 mg, 0.65 mmol), anhydrous barium carbonate (153 mg, 0.78 mmol), and p-nitroaniline (0.78 mmol) in 7 mL of dry 1,2,-dichloroethane under nitrogen was stirred overnight at room temperature. The reaction mixture was filtered, diluted, washed with water, dried over magnesium sulfate, and purified by column chromatography (30 g silica gel with dichloromethane-acetone-ethyl acetate 100:5:5 or toluene-ethyl acetate 3:1 as an eluent), generally according to published methods (Wang, 1990a). Yield of the 4"-O-Demethyl- 4β-[4"nitroanilino]-4-desoxypodophyllotoxin (compound 13, FIG. 5) was 44%. The compound recrystallized from EtOAc is characterized by: mp 205°–207° C.; [α]$^{25}_D$–170° (c=0.5, CHCl$_3$); IR (KBr) 3500 (OH), 3470 (NH), 2920 (aliphatic C—H), 1775 (lactone), 1600, 15520 and 1490 (aromatic C===C), 1330 and 1310 (NO$_2$) cm$^{-1}$; $^1$H NMR (CDCl$_3$) δ 8.15 (d, J=9.1 Hz, 2 H, 3", 5"-H), 6.76 (s, 1 H, 5-H), 6.60 (d, 3 H, 8-H and 2", 6"-H), 6.32 (s, 2 H, 2", 6"-H),6.00 (s, 1 H, OCH$_2$O), 5.98 (s, 1 H, OCH$_2$O), 5.46 (s, 1 H, 4"-OH), 4.83 (m, 1 H, NH), 4.62 (m, 2 H, 4-H and 1-H), 4.41 (t, 1 H, 11-H), 3.90 (t, 1 H, 11-H), 3.80 (s, 6 H, 3', 5'-OCH$_3$), 3.10 (m, 2 H, 2-H and 3-H).

Anal: (C$_{27}$H$_{24}$N$_2$O$_9$) C, H, N.

B. Synthesis of 4'-O-Demethyl-4β-[6 4"-aminoanilino]-4 -desoxypodophyllotoxin (compound 14)

To a solution of 4'-O-Demethyl-4β-[4"-nitroanilino]-4 -desoxypodophyllotoxin (900 mg, 1.73 mmol), and 10% palladium on activated carbon (450 mg) in 100 ml ethyl acetate was introduced hydrogen gas for 5 hours. The solution was then filtered, and the filtrate was evaporated to dryness. The crude product was crystallized with methanol to yield (4'-O-Demethyl-4β-[4"-aminoanilino]-4 -desoxypodophyllotoxin, compound 14, FIG. 5). Compound yield to 72%.

The compound has the NMR characteristics: (CDCl$_3$) δ 6.77 (s, 1 H, H-5), 6.64 (d, J=8.7 Hz, 2 H, H-3",5"), 6.52 (s, 1 H, H-8), 6.42 (d, J 8.7 Hz, 2 H, H-3",6"), 5.96 and 5.97 (s and s, 2 H, OCH$_2$O), 4.59 (d, J=5.0 Hz, 1 H, H-1), 4.56 and 4.37 (t and t, 2 H, H-11 and H-11'), 3.80 (s, 6H, OCH$_3$-3',5'), 3.18 (dd, J=5.0, 15.0 Hz, 1 H, H-2), 2.96 (m, 1 H, H-3).

Anal. ($C_{27}H_{26}N_2O_7 \cdot H_2O$) C, H.

C. Synthesis of 4'-O-Demethyl-4β-[4"-dimethylaminoanilino]-4-desoxypodophyllotoxin (compound 15)

To a solution of 4'-O-Demethyl-4β-[4-aminoanilino]-4 -desoxypodophyllotoxin (530 mg, 1.08 mmol) in 10 ml dichloromethane was added 37% formaldehyde (350 μl, 4.32 mmol), and sodium cyanoborohydride (214 mg, 4.24 mmol). The reaction mixture was stirred at room temperature for 10 minutes, then diluted with ethyl acetate and washed with water. The organic layer was dried over magnesium sulfate and evaporated to dryness. The crude product was purified by flash column chromatography with CH$_2$Cl$_2$:MeOH:acetone (80:1.5:4) as eluant to yield 200 mg of product 4'-O-Demethyl-4 β-[4"-dimethylaminoanilino]-4 -desoxypodophyllotoxin. The yield was 36%.

The compound has the NMR characteristics: δ 6.78 (s, 1 H, H-5), 6.75 (d, J=9.0 Hz, 2 H, H-3",5"), 6.52 (s, 1 H, H-8), 6.51 (d, J=9.0 Hz, 2 H, H-2",6"), 6.34 (s, 2 H, H-2',6'), 5.97 and 5.95 (s and s, 2 H, OCH$_2$O), 5.44 (s, 1 H, OH-4'), 4.60 and 4.59 (s and s, brs, 2H, H-1 and H-4), 4.37 and 4.06(t and t, 2 H, H-11 and H-11'), 3.80 (s, 6 H, OCH$_3$3',5'), 3.48 (brs, 1 H, NH-4), 3.19 (dd, J=5.0, 15.0 Hz, 1 H, H-2), 2.98 (m, 1 H, H-3), 2.90 (s, 6 H, NCH$_3$-4").

D. Synthesis of 4'-O-Demethyl-4β-N-methyl, —(4"-N',N'dimethylamino)anilino-4-desoxypodophyllotoxin (Compound 17).

To a solution of compound 13 (2 g, 3.84 mmol), 10% palladium on activated carbon (1 g) in 150 ml of ethyl acetate and 3 ml of acetic acid was introduced hydrogen gas at an atmospheric pressure for 48 hr. The reaction mixture was filtered on a pad of silica gel and washed with EtOAc:meOH (5:1). The filtrate was concentrated under reduced pressure to leave an oil (containing compound 14) which was used for the next step of the reaction without purification. The above oil was dissolved in 20 ml of MeOH and added with 37% of formaldehyde (1 ml). The resulting mixture was stirred at room temperature for 10 min. Sodium cyanoborohydride (1 g) was added portwise during 30 min. The solvent was then removed under reduced pressure and the residue was made alkaline with 5% NaHCO$_3$, extracted with chloroform. The extract was washed with brine, dried over MgSO$_4$, and evaporated in vacuo to leave an oily residue, which was subject to flash chromatograph with EtOAc/Hexane as an eluant. The pure compound 17 (330 mg) was obtained. Yield: 17%.

NMR characteristics were: $^1$H NMR (CDCl$_3$) δ 6.82 (d, J=9.0 Hz, 2 H, H-2",6"), 6.74 (s, 1 H, H-5), 6.69 (d, J=9.0 Hz, 2 H, H-3",5"), 6.57 (s, 1 H, H-8), 6.34 (s, 2 H, H- 2',6'), 5.97 (s, 2H, OCH$_2$O), 5.42 (s, 1 H, OH-4'), 5.08 (d, J=5.3 Hz, 1 H, H-4), 4.65 (d, J=4.7 Hz, 1 H, H-1), 4.28 and 3.90 (t and t, 2 H, H-11 and H-11'), 3.79 (s, 6H, OCH$_3$- 3',5'), 3.08 (dd, J=4.7, 9.8 hz, 1 H, H-2), 2.95 (m, 1 H, H-3), 2.87 [s, 6H, N(CH$_3$)$_2$-4"], 2.69 (s, 3H, NCH$_3$-4).

E. Synthesis of HCl Salts of Compounds 15 and 17

A solution of compound 15 or compound 17 in methanol was adjusted with hydrogen chloride solution in ethanol to pH=1–2. The resulting solution was evaporated in vacuo to dryness. The residue was washed with ethyl ether to drive the free hydrogen chloride away until approximately neutral pH.

4'-O-Demethyl-4β-(4"-dimethylaminoanilino)-4-desoxypodophyllotoxin Hydrochloride (Compound 16) was charactertized as follows: mp 185°–188° C.; [α]$^{25}_D$ –109 (c=0.2, MeOH); IR (KBr) 3396, 2903, 1772, 1611, 1517 and 1483 cm$^{-1}$; $^1$H NMR (CD$_3$OD) δ 7.90 (s, 1 H, OH-4'), 7.40 (d, J=8.7 Hz, 2 H, H-3",5"), 6.82 (d, J=8.7 Hz, 2 H, H-2",6"), 6.73 (s, 1 H, H-5), 6.52 (s, 1 H, H-8), 6.37 (s, 2 H, H-2',6'), 5.94 (s, 2 H, OCH$_2$O), 4.60 (d, J=4.8 Hz, 1 H, H-4), 4.41 (t, 1 H, H-11), 3.82 (m, 2H, H-1 and H-11'), 3.74 (s, 6H, OCH$_3$-3', 5'), 3.25 [s, 6H, N(CH$_3$)$_2$-4"], 3.13 (m, 1H, H-3).

Anal. ($C_{29}H_{30}N_2O_7 \cdot HCl \cdot 3H_2O$) C, H, N.

4'-O-Demethyl-4β-N-methyl-(4"-dimethyl N', N'-amino)anilino-4-desoxy-podophyllotoxin Hydrochloride (compound 18) was characterized as follows: mp 137°–141° C.; [α]$^{25}_D$+260 (c=0.25, MeOH); IR (KBr) 3402, 2906, 2904, 1775, 1610, 1518, and 1482 cm$^{-1}$; $^1$H NMR (CD$_3$OD) δ 7.52 (d, J=9.1 Hz, 2 H, H-3",5"), 7.04 (d, J=9.1 Hz, 2 H, H-3",5"), 6.61 (s, 1 H, H-5), 6.57 (s, 1 H, H-8), 6.39 (s, 2 H, H-2',6'), 5.98 (s, 2H, OCH$_2$O), 4.70 (d, J=4.8 Hz, 1 H, H-4), 4.38 (t, 1 H, H-11), 3.71 (s, 6H, OCH$_3$-3',5'), 3.17 [s, 6H, N(CH$_3$)$_2$-4"], 2.77 (s, 3 H, NCH$_3$-4).

Anal. ($C_{30}H_{32}N_2O_7 \cdot HCl \cdot 11/2H_2O$) C, H, N, Cl.

Example 5

Synthesis of 4'-O-Demethyl-4β-[4"-dimethylaminoanilino]-4-desoxypodophyllotoxin: Method 2

To 4'-O-Demethyl-4β-bromo-4-desoxypodophyllotoxin (1.13 g) (compound 2 FIG. 6) dissolved in dry 1,2 dichloroethane (8 ml) was added BaCO$_3$ (987 mg) and then a dry ClCH$_2$CH$_2$Cl solution (2 ml) of p-dimethylaminoaniline (681 mg) (compound 19) with ice bath cooling. After overnight stirring at 0° C., the suspension was filtered and the filtered solid rinsed with CH$_2$Cl$_2$. The combined filtrates were extracted with water, dried over Na$_2$SO$_4$, and filtered. After concentration in vacuo of the filtrate, the residue was chromatographed on SiO$_2$ column using ether/CH$_2$Cl$_2$ solvent system. After concentration of the eluent in vacuo, final purification by several recrystallizations from CH$_2$Cl$_2$ yield the final product (231 mg).

Example 6

Biological Evaluation of Topoisomerase Analog Compounds

A. Topoisomerase II activity.

Human DNA topoisomerase II was isolated from peripheral blast cells of a patient with acute leukemia. The isolation procedure has been described (Thurston, 1988). A test compound (4-a)–(4-t) was dissolved in dimethylsulfoxide at a concentration of 20 mM as a stock solution and diluted before use with water to a desired concentration of compound.

The P4 unknotting reaction was a modification of the procedure described by Liu (1981). The reaction mixture (20 μL), which contained 50 mM HEPES, pH 7.0, 50 mM KCl, 100 mM NaCl, 0.1 mM EDTA, 10 mM $MgCl_2$, 1.0 mM ATP, 50 μg/mL bovine serum albumin, 0.4 μg P4 knotted DNA, and enzyme, was incubated with or without drugs.

The reaction mixture was incubated at 37° C. for 30 min and terminated by adding 5.0 μl of a stop solution (2% sodium dodecyl sulfate, 20% glycerol, 0.05% bromophenol blue). These samples were loaded onto a 1% agarose gel and electectrophoresed at 55 V overnight with an electrophoresis buffer that contained 90 mM Tris-boric acid, pH 8.3, and 2.5 mM EDTA. At completion, the gel was stained in 0.5 μg/mL of ethidium bromide. Then a photograph was taken of the DNA bands visualized with fluorescence induced by a long-wavelength UV lamp. The data reported in Table 1 reflect a 100 mM drug concentration.

B. Cellular Protein-DNA Complex Formation

The intracellular formation of covalent topoisomerase II-DNA complexes was quantitated using the potassium SDS precipitation assay, a procedure adapted from the method described in Rowe et al. (1986) which is herein specifically incorporated by reference. KB ATCC cells were prelabeled with 0.05 mci/ml $^{14}$C-thymidine (specific activity 50.5 mci-mmol) for 18 hr. A final concentration of $5\times10^5$ cells/sample were treated with 10 μM of the drugs at 37° C. for 1 hr and proceeded according to the procedure described by Rowe et al. to detect the protein linked DNA levels.

It will be apparent to those skilled in the art that various modifications and variations can be made in the processes and products of the present invention. Thus, it is intended that the present invention cover the modifications and variations of this invention provided that they come within the scope of the appended claims and their equivalents.

It is claimed:

1. A 4β-amino podophyllotoxin analog compound of the formula:

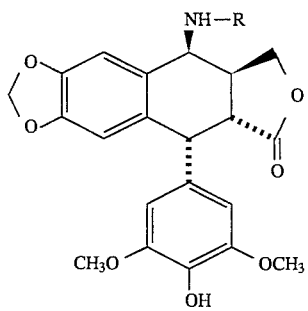

(I)

wherein NH—R is selected from the group consisting of:
(a) NH—$(CH_2)_n$—$NR_1R_2$, or (b) 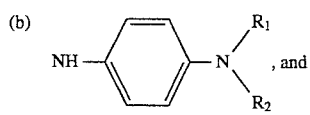 , and (c) an aryl amine of the form:

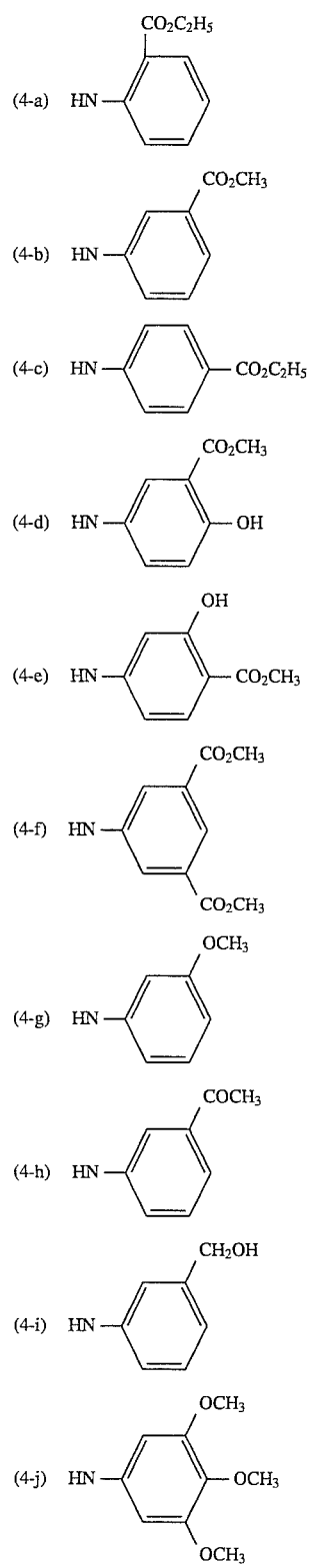

-continued

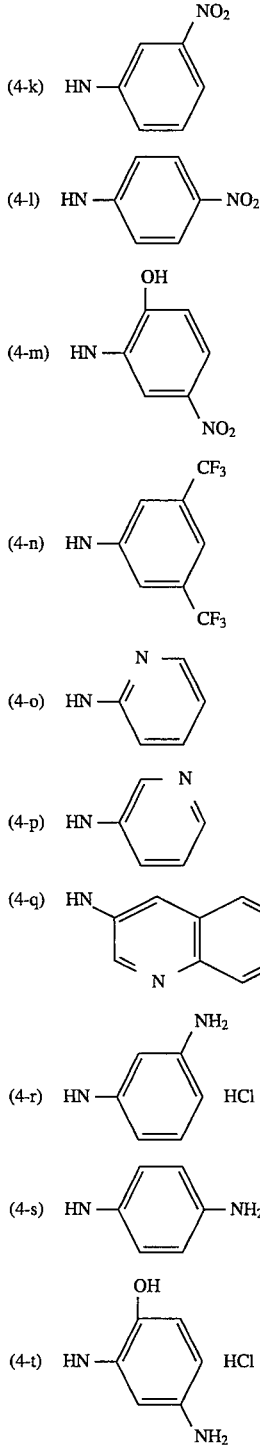

including ammonium salts of structures (a), (b) and (c), where $R_1$ and $R_2$ in structures (a) and (b) are H or methyl groups and n is an integer from 2 to 4.

2. The compound of claim 1, wherein NH—R is —NH(CH$_2$)$_2$N(CH$_3$)$_2$.

3. The compound of claim 1, wherein NH—R is —NH(CH$_2$)$_3$N(CH$_3$)$_2$.

4. The compound of claim 1, wherein NH—R is —NH(CH$_2$)$_4$N(CH$_3$)$_2$.

5. The compound of claim 1, wherein NH—R has the form

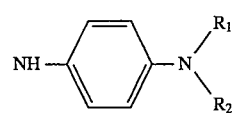

6. The compound of claim 5, wherein $R_1$ and $R_2$ are each CH$_3$.

7. The compound of claim 1, wherein NH—R is selected from the group consisting of:

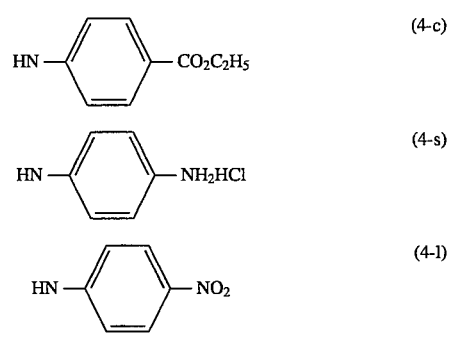

8. The compound of claim 7, wherein NH—R has the form:

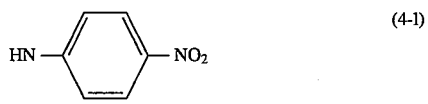

9. A pharmaceutical composition comprising the compound of claim 7, and a pharamaceutically acceptable carrier.

10. A pharmaceutical composition comprising the compound of claim 1, and a pharamaceutically acceptable carrier.

* * * * *